US008468029B2

(12) United States Patent
Jung et al.

(10) Patent No.: US 8,468,029 B2
(45) Date of Patent: Jun. 18, 2013

(54) SUBSCRIPTIONS FOR ASSISTANCE RELATED TO HEALTH

(75) Inventors: Edward K. Y. Jung, Las Vegas, NV (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 935 days.

(21) Appl. No.: 11/314,764

(22) Filed: Dec. 21, 2005

(65) Prior Publication Data

US 2007/0112590 A1    May 17, 2007

Related U.S. Application Data

(63) Continuation-in-part of application No. 11/314,949, filed on Dec. 21, 2005, which is a continuation-in-part of application No. 11/285,753, filed on Nov. 22, 2005, which is a continuation-in-part of application No. 11/285,500, filed on Nov. 22, 2005, which is a continuation-in-part of application No. 11/283,548, filed on Nov. 17, 2005.

(51) Int. Cl.
*G06Q 10/00* (2012.01)
(52) U.S. Cl.
USPC .................................... 705/2; 705/3; 600/300
(58) Field of Classification Search
USPC .......................................... 705/2, 3; 600/300
See application file for complete search history.

(56) References Cited

U.S. PATENT DOCUMENTS

| 4,838,275 A | 6/1989 | Lee |
| 4,847,764 A | 7/1989 | Halvorson |
| 4,857,716 A | 8/1989 | Gombrich et al. |
| 5,054,493 A | 10/1991 | Cohn et al. |
| 5,279,294 A | 1/1994 | Anderson et al. |
| 5,300,302 A | 4/1994 | Tachon et al. |
| 5,307,263 A | 4/1994 | Brown |
| 5,495,961 A | 3/1996 | Maestre |
| 5,537,313 A | 7/1996 | Pirelli |
| 5,672,154 A | 9/1997 | Sillén et al. |
| 5,700,998 A | 12/1997 | Palti |

(Continued)

FOREIGN PATENT DOCUMENTS

| WO | WO 99/45354 | 9/1999 |
| WO | WO 00/60362 | 10/2000 |

(Continued)

OTHER PUBLICATIONS

PCT International Search Report; International App. No. PCT/US07/25379; May 13, 2008; pp. 1-2.

(Continued)

*Primary Examiner* — Lena Najarian

(57) ABSTRACT

An interactive network-based health-related data management system provides provisions of health regimen information from an end-user and/or vendor and/or publisher. In an implementation, a subscription data for one or more subscriptions for the health regimen information is accepted by the system. To this end, the system provides the health regimen information according to the subscription data pertaining to the end/user and/or the vendor and/or the publisher.

22 Claims, 17 Drawing Sheets

U.S. PATENT DOCUMENTS

| | | | |
|---|---|---|---|
| 5,710,578 | A | 1/1998 | Beauregard et al. |
| 5,737,539 | A | 4/1998 | Edelson et al. |
| 5,770,226 | A | 6/1998 | Hughes, Jr. et al. |
| 5,940,801 | A | 8/1999 | Brown |
| 5,954,640 | A | 9/1999 | Szabo |
| 5,955,269 | A | 9/1999 | Ghai et al. |
| 5,995,938 | A | 11/1999 | Whaley |
| 6,021,202 | A | 2/2000 | Anderson et al. |
| 6,117,073 | A | 9/2000 | Jones et al. |
| 6,139,494 | A | 10/2000 | Cairnes |
| 6,188,988 | B1 | 2/2001 | Barry et al. |
| 6,209,095 | B1 | 3/2001 | Anderson et al. |
| 6,227,371 | B1 | 5/2001 | Song |
| 6,287,595 | B1 | 9/2001 | Loewy et al. |
| 6,397,190 | B1 | 5/2002 | Goetz |
| 6,421,650 | B1 | 7/2002 | Goetz et al. |
| 6,450,956 | B1 | 9/2002 | Rappaport et al. |
| 6,510,430 | B1 | 1/2003 | Oberwager et al. |
| 6,529,446 | B1 | 3/2003 | de la Huerga |
| 6,609,200 | B2 | 8/2003 | Anderson et al. |
| 6,656,122 | B2 | 12/2003 | Davidson et al. |
| 6,671,818 | B1 | 12/2003 | Mikurak |
| 6,699,193 | B2 | 3/2004 | Crutchfield et al. |
| 6,764,831 | B2 | 7/2004 | Cameron, Sr. et al. |
| 6,770,029 | B2 | 8/2004 | Iliff |
| 6,790,198 | B1 | 9/2004 | White et al. |
| 6,898,761 | B2 | 5/2005 | Johnson |
| 6,955,873 | B1 | 10/2005 | Blum |
| 7,005,447 | B2 | 2/2006 | Ahotupa et al. |
| 7,016,752 | B1 | 3/2006 | Ruben et al. |
| 7,135,616 | B2 | 11/2006 | Heard et al. |
| 7,136,820 | B1 | 11/2006 | Petrus |
| 7,169,432 | B2 | 1/2007 | Tanaka et al. |
| 7,172,897 | B2 | 2/2007 | Blackburn et al. |
| 7,193,128 | B2 | 3/2007 | Copenhaver et al. |
| 7,197,492 | B2 | 3/2007 | Sullivan |
| 7,216,343 | B2 | 5/2007 | Das et al. |
| 7,280,975 | B1 | 10/2007 | Donner |
| 7,351,739 | B2 | 4/2008 | Ho et al. |
| 7,376,585 | B2 | 5/2008 | Haller |
| 7,418,399 | B2 | 8/2008 | Schaeffer et al. |
| 7,483,839 | B2 | 1/2009 | Mayaud |
| 7,490,085 | B2 | 2/2009 | Walker et al. |
| 7,502,666 | B2 | 3/2009 | Siegel et al. |
| 2001/0039503 | A1 | 11/2001 | Chan et al. |
| 2002/0027164 | A1 | 3/2002 | Mault et al. |
| 2002/0032580 | A1* | 3/2002 | Hopkins ............................ 705/2 |
| 2002/0065682 | A1* | 5/2002 | Goldenberg ....................... 705/2 |
| 2002/0091546 | A1 | 7/2002 | Christakis et al. |
| 2002/0099686 | A1 | 7/2002 | Schwartz et al. |
| 2002/0106429 | A1 | 8/2002 | Mudar et al. |
| 2002/0111932 | A1 | 8/2002 | Roberge et al. |
| 2002/0116225 | A1 | 8/2002 | Morse et al. |
| 2002/0128259 | A1 | 9/2002 | Ghazzi et al. |
| 2002/0147317 | A1 | 10/2002 | Bentsen et al. |
| 2002/0156651 | A1* | 10/2002 | Florio et al. ...................... 705/2 |
| 2002/0192310 | A1 | 12/2002 | Bland et al. |
| 2002/0194221 | A1 | 12/2002 | Strong et al. |
| 2003/0004403 | A1 | 1/2003 | Drinan et al. |
| 2003/0028399 | A1 | 2/2003 | Davis et al. |
| 2003/0036683 | A1* | 2/2003 | Kehr et al. ...................... 600/300 |
| 2003/0046114 | A1 | 3/2003 | Davies et al. |
| 2003/0069757 | A1 | 4/2003 | Greenberg |
| 2003/0082544 | A1 | 5/2003 | Fors et al. |
| 2003/0114475 | A1 | 6/2003 | Fox et al. |
| 2003/0135388 | A1 | 7/2003 | Martucci et al. |
| 2003/0139655 | A1 | 7/2003 | Dodds |
| 2003/0158756 | A1 | 8/2003 | Abramson |
| 2003/0204412 | A1 | 10/2003 | Brier |
| 2003/0229455 | A1 | 12/2003 | Bevilacqua et al. |
| 2003/0233250 | A1 | 12/2003 | Joffe et al. |
| 2004/0064342 | A1 | 4/2004 | Browne et al. |
| 2004/0088374 | A1 | 5/2004 | Webb et al. |
| 2004/0111298 | A1 | 6/2004 | Schoenberg |
| 2004/0121767 | A1 | 6/2004 | Simpson et al. |
| 2004/0122707 | A1* | 6/2004 | Sabol et al. ...................... 705/2 |
| 2004/0122790 | A1 | 6/2004 | Walker et al. |
| 2004/0138926 | A1 | 7/2004 | Ishikawa et al. |
| 2004/0143403 | A1 | 7/2004 | Brandon et al. |
| 2004/0176984 | A1 | 9/2004 | White et al. |
| 2004/0215486 | A1 | 10/2004 | Braverman |
| 2004/0243437 | A1 | 12/2004 | Grace et al. |
| 2004/0243441 | A1* | 12/2004 | Bocionek et al. ................. 705/2 |
| 2004/0254868 | A1 | 12/2004 | Kirkland et al. |
| 2005/0027570 | A1 | 2/2005 | Maier et al. |
| 2005/0033121 | A1* | 2/2005 | Modrovich ................... 600/300 |
| 2005/0033773 | A1 | 2/2005 | Roberge et al. |
| 2005/0038558 | A1 | 2/2005 | Keene |
| 2005/0061336 | A1 | 3/2005 | Goetz et al. |
| 2005/0090718 | A1 | 4/2005 | Dodds |
| 2005/0101841 | A9 | 5/2005 | Kaylor et al. |
| 2005/0102159 | A1 | 5/2005 | Mondshine |
| 2005/0118202 | A1 | 6/2005 | Yamashita et al. |
| 2005/0147667 | A1 | 7/2005 | Rines |
| 2005/0192487 | A1 | 9/2005 | Cosentino et al. |
| 2005/0216313 | A1 | 9/2005 | Claud et al. |
| 2005/0216390 | A1 | 9/2005 | Snider et al. |
| 2005/0256745 | A1 | 11/2005 | Dalton |
| 2005/0260610 | A1 | 11/2005 | Kurtz et al. |
| 2005/0260679 | A1 | 11/2005 | Kellerman et al. |
| 2005/0261255 | A1 | 11/2005 | Serhan et al. |
| 2005/0267356 | A1 | 12/2005 | Ramasubramanian et al. |
| 2005/0271596 | A1 | 12/2005 | Friedman et al. |
| 2006/0047538 | A1 | 3/2006 | Condurso et al. |
| 2006/0064250 | A1 | 3/2006 | Goldstein |
| 2006/0090765 | A1 | 5/2006 | Surina |
| 2006/0111944 | A1* | 5/2006 | Sirmans et al. ................... 705/3 |
| 2006/0129324 | A1 | 6/2006 | Rabinoff et al. |
| 2006/0161443 | A1 | 7/2006 | Rollins |
| 2006/0177637 | A1 | 8/2006 | Kimura |
| 2006/0248468 | A1 | 11/2006 | Constantine et al. |
| 2006/0254580 | A1 | 11/2006 | Chalmers et al. |
| 2006/0260679 | A1 | 11/2006 | Aratani et al. |
| 2006/0287891 | A1 | 12/2006 | Grasso et al. |
| 2007/0035403 | A1 | 2/2007 | Krishna et al. |
| 2007/0068959 | A1 | 3/2007 | D'Silva |
| 2007/0087048 | A1 | 4/2007 | Abrams et al. |
| 2007/0136092 | A1 | 6/2007 | Jung et al. |
| 2007/0161076 | A1 | 7/2007 | Halden |
| 2008/0097784 | A1 | 4/2008 | Miller et al. |
| 2008/0139907 | A1 | 6/2008 | Rao et al. |
| 2008/0299013 | A1 | 12/2008 | Trieu et al. |
| 2010/0081144 | A1 | 4/2010 | Holmes et al. |

FOREIGN PATENT DOCUMENTS

| | | | |
|---|---|---|---|
| WO | WO 01/79529 | A1 | 10/2001 |
| WO | WO 2005/062849 | A2 | 7/2005 |
| WO | WO 2007/061838 | A2 | 5/2007 |

OTHER PUBLICATIONS

PCT International Search Report; International App. No. PCT/US07/25417; May 14, 2008; pp. 1-3.

PCT International Search Report; International App. No. PCT/US07/25417; May 19, 2008; pp. 1-2.

PCT International Search Report; International App. No. PCT/US2007/025450; May 23, 2008; pp. 1-2.

PCT International Search Report; International App. No. PCT/US06/47835; Jul. 14, 2008; pp. 1-2.

U.S. Appl. No. 11/355,517, Jung et al.

U.S. Appl. No. 11/339,316, Jung et al.

U.S. Appl. No. 11/314,949, Jung et al.

U.S. Appl. No. 11/314,945, Jung et al.

U.S. Appl. No. 11/291,532, Jung et al.

U.S. Appl. No. 11/291,482, Jung et al.

PCT International Search Report; International App. No. PCT/US 06/44664; Apr. 14, 2008; pp. 1-3.

PCT International Search Report; International App. No. PCT/ US 06/44278; 2 pages; Aug. 17, 2007.

PCT International Search Report; International App. No. PCT/ US 06/44269; 2 pages; Sep. 18, 2007.

Cover, Robin, ed.; "Technology Reports: General SGML/XML Applications" [see e.g. "SGML Initiative in Health Care (HL7 Health Level-7 and SGML/XML)"]; Cover Pages: Hosted by Oasis; Bearing a date of Nov. 11, 2002, printed on Nov. 16, 2005; pp. 1-95; located at: http://xml.coverpages.org/gen-apps.html.

Goedert, Joseph, ed.; "XML Comes of Age for Data Exchange"; Health Data Management; Bearing dates of Nov. 16, 2005 and 2005, printed on Nov. 16, 2005; pp. 1-4; SourceMedia, Inc; located at: http://www.healthdatamanagement.com/html/current/CurrentIssueStory.cfm?PostID=16205.

Guo, Jinqiu; Araki, Kenji; Tanaka, Koji; Sato, Junzo; Suzuki, Muneou; Takada, Akira; Suzuki, Toshiaki; Nakashima, Yusei; Yoshihara, Hiroyuki; "The Latest MML (Medical Markup Language) Version 2.3—XML-Based Standard for Medical Data Exchange/Storage"; Journal of Medical Systems; Bearing dates of Aug. 2003 and 2003; printed on Nov. 16, 2005; pp. 357-366; vol. 27, No. 4; Plenum Publishing Corporation; located at: http://lob.kuhp.kyoto-u.ac.jp/paper/200308mml23JMS/mml23JMS.pdf.

Kahn Jr., Charles E.; De La Cruz, Norberto B.; "Extensible Markup Language (XML) in Health Care: Integration of Structured Reporting and Decision Support"; Office of Clinical Informatics; printed on Nov. 16, 2005; pp. 1-5; located at: http://www.amia.org/pubs/symposia/D004673.PDF.

McDonald, Carol; Srinivas, Raghavan N.; "How Java Technology and XML are Improving Healthcare in Brazil"; Java.sun.com; Bearing dates of Feb. 2004 and 1994-2005, printed on Nov. 16, 2005; pp. 1-9; Sun Microsystems, Inc.; located at: http://java.sun.com/developer/technicalArticles/xml/brazil/index.html.

Smith, Stevie; "New Chip Identifies Bird Flu in Humans"; The Tech Herald.com, WOTR Limited; 2008; located at: www.thetechherald.com/article/php200813/520/new-chip-identifies-bird-flu-in-humans; Bearing a date of Mar. 25, 2008; printed on Sep. 8, 2008; pp. 1-6.

PCT International Search Report; International App. No. PCT/US2007/025451; Sep. 15, 2008; pp. 1-2.

PCT International Search Report; International App. No. PCT/US07/20272; Sep. 15, 2008; pp. 1-2.

PCT International Search Report; International App. No. PCT/US07/20305; Sep. 11, 2008; pp. 1-2.

PCT International Search Report; International App. No. PCT/US07/20283; Sep. 11, 2008; pp. 1-2.

PCT International Search Report; International App. No. PCT/US07/14994; Sep. 9, 2008; pp. 1-2.

PCT International Search Report; International App. No. PCT/US2008/007993; Sep. 8, 2008; pp. 1-3.

PCT International Search Report; International App. No. PCT/US06/47451; Sep. 5, 2008; pp. 1-2.

PCT International Search Report; International App. No. PCT/US06/44658; Aug. 29, 2008; pp. 1-2.

PCT International Search Report; International App. No. PCT/US06/44279; Aug. 19, 2008; pp. 1-3.

PCT International Search Report; International App. No. PCT/US06/44283; Aug. 18, 2008; pp. 1-2.

PCT International Search Report; International App. No. PCT/US07/14266; Jul. 21, 2008; pp. 1-2.

Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.

Sriskanthan, N. and Subramanian, K. R.; "Braille Display Terminal for Personal Computers"; IEEE Transactions on Consumer Electronics; May 1990; pp. 121-128; vol. 36, No. 2; IEEE.

UK Intellectual Property Office Examination Report Under Section 18(3); App. No. GB1000316.8; Jul. 26, 2011; pp. 1-3.

Walt et al.; "Biological Warfare, A Host of Detection Strategies Have Been Developed, But Each Has Significant Limitations"; Analytical Chemistry; bearing a date of Dec. 1, 2000; pp. 738A-747A.

U.S. Appl. No. 13/374,765, Jung et al.

\* cited by examiner

SUBSCRIPTIONS FOR ASSISTANCE RELATED TO HEALTH

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. Stephen G. Kunin, *Benefit of Prior-Filed Application*, USPTO Electronic Official Gazette, Mar. 18, 2003 at http://www.uspto.gov/web/offices/com/sol/og/2003/week 11/patbene.htm. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

RELATED APPLICATIONS

1. For purposes of the USPTO extra-statutory requirements, the present application constitutes a continuation in part of currently co-pending United States patent application entitled Providing Assistance Related to Health, naming Edward K. Y. Jung, Royce A. Levien, Robert W. Lord, Mark A. Malamud, John D. Rinaldo, Jr., and Lowell L. Wood, Jr., as inventors, U.S. Ser. No. 11/283,548, filed Nov. 17, 2005.
2. For purposes of the USPTO extra-statutory requirements, the present application constitutes a continuation in part of currently co-pending United States patent application entitled User Interface for Providing Assistance Related to Health, naming Edward K.Y. Jung, Royce A. Levien, Robert W. Lord, Mark A. Malamud, John D. Rinaldo, Jr., and Lowell L. Wood, Jr., as inventors, U.S. Ser. No. 11/285, 753, filed Nov. 22, 2005.
3. For purposes of the USPTO extra-statutory requirements, the present application constitutes a continuation in part of currently co-pending United States patent application entitled User Interface for Providing Assistance Related to Health, naming Edward K.Y. Jung, Royce A. Levien, Robert W. Lord, Mark A. Malamud, John D. Rinaldo, Jr., and Lowell L. Wood, Jr., as inventors, U.S. Ser. No. 11/285, 500, filed Nov. 22, 2005.
4. For purposes of the USPTO extra-statutory requirements, the present application constitutes a continuation in part of currently co-pending United States patent application entitled Research in Providing Assistance Related to Health, naming Edward K. Y. Jung, Royce A. Levien, Robert W. Lord, Mark A. Malamud, John D. Rinaldo, Jr., and Lowell L. Wood, Jr., as inventors, USAN: [To be Assigned], filed substantially contemporaneously herewith.

TECHNICAL FIELD

The present application relates, in general, to health-related data management.

SUMMARY

In one aspect, a method related to health-related data management includes but is not limited to accepting subscription data for one or more subscriptions for provision of health regimen information from an end-user and/or vendor and/or publisher. In addition to the foregoing, other method aspects are described in the claims, drawings, and text forming a part of the present application.

In one aspect, a method related to health-related data management includes but is not limited to providing health regimen information according to subscription data pertaining to an end-user and/or vendor and/or publisher. In addition to the foregoing, other method aspects are described in the claims, drawings, and text forming a part of the present application.

In one aspect, a system related to health-related data management includes but is not limited to circuitry for accepting subscription data for one or more subscriptions for provision of health regimen information from an end-user and/or vendor and/or publisher. In addition to the foregoing, other system aspects are described in the claims, drawings, and text forming a part of the present application.

In another aspect, a system related to health-related data management includes but is not limited to circuitry for providing health regimen information according to subscription data pertaining to an end-user and/or vendor and/or publisher. In addition to the foregoing, other system aspects are described in the claims, drawings, and text forming a part of the present application.

In one or more various aspects, related systems include but are not limited to circuitry and/or programming and/or electro-mechanical devices and/or optical devices for effecting the herein-referenced method aspects; the circuitry and/or programming and/or electro-mechanical devices and/or optical devices can be virtually any combination of hardware, software, and/or firmware configured to effect the herein-referenced method aspects depending upon the design choices of the system designer skilled in the art.

In one aspect, a program product includes but is not limited to a signal bearing medium bearing one or more instructions for accepting subscription data for one or more subscriptions for provision of health regimen information from an end-user and/or vendor and/or publisher. In addition to the foregoing, other program product aspects are described in the claims, drawings, and text forming a part of the present application.

In another aspect, a program product includes but is not limited to a signal bearing medium bearing one or more instructions for providing health regimen information according to subscription data pertaining to an end-user and/ or vendor and/or publisher. In addition to the foregoing, other program product aspects are described in the claims, drawings, and text forming a part of the present application.

In addition to the foregoing, various other method, system, and/or program product aspects are set forth and described in the teachings such as the text (e.g., claims and/or detailed description) and/or drawings of the present application.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

The use of the same symbols in different drawings typically indicates similar or identical items.

DETAILED DESCRIPTION

Figure 1:
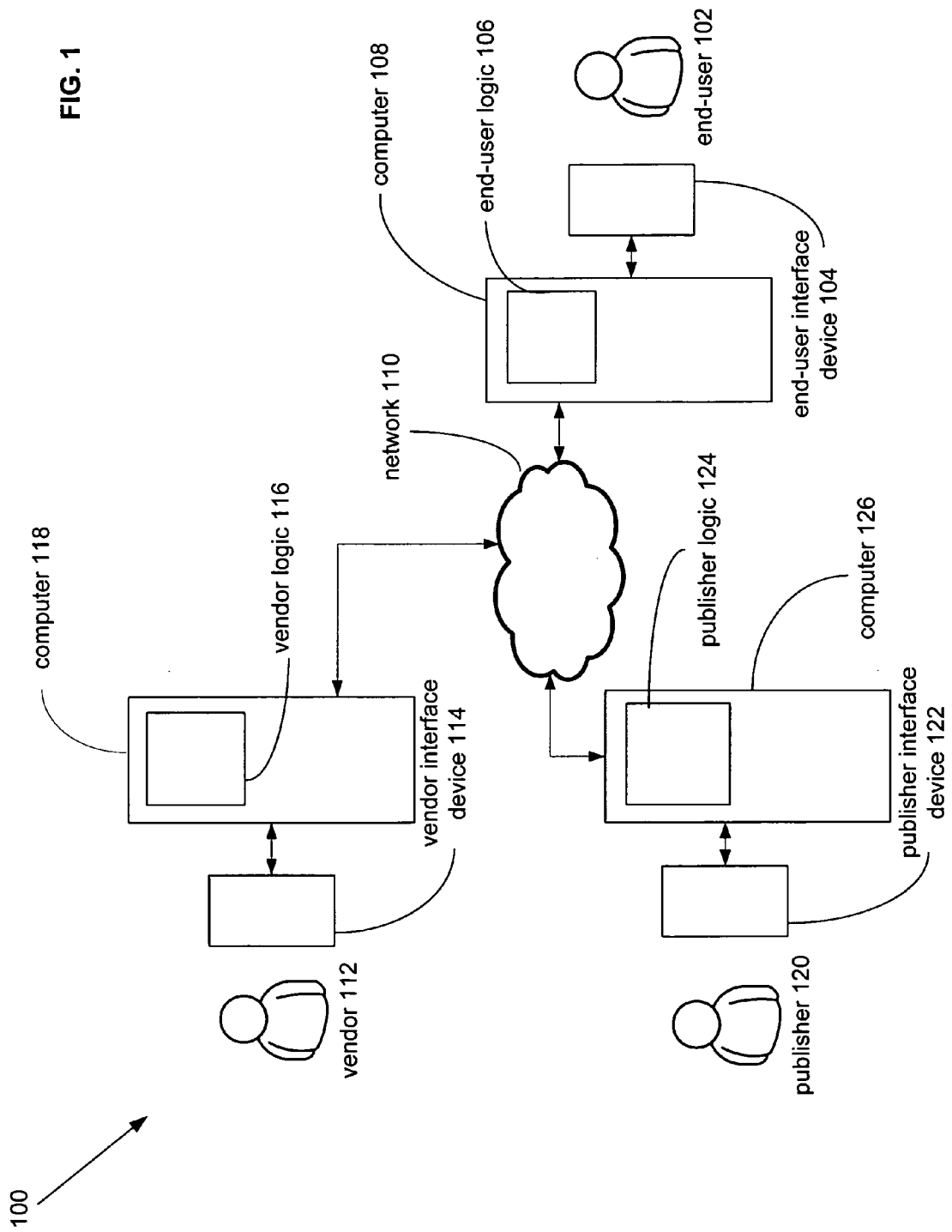
FIG. 1 depicts one implementation of an exemplary environment in which the methods and systems described herein may be represented.

FIG. 1 illustrates an exemplary environment 100 in which embodiments may be used. The end-user 102 is a person who wishes to access information regarding pharmaceutical, nutraceutical, veterinary, dietary, and/or nutritional substances, procedures, processes, and/or practices of interest for use in a health regimen or regimens. The end-user interface device 104 may be a keyboard, mouse, trackball, monitor, microphone and speakers, and/or other interface device or devices for a human to interface with the end-user logic 106 of computer 108. The end-user logic 106 may include at least a portion of the hardware/software/firmware of the computer 108. The computer 108 may be used by the end-user 102 to access such information via another computer or computers represented by the network 110.

Vendor 112 is a person and/or persons and/or entity and/or entities that may supply pharmaceutical, nutraceutical, veterinary, dietary, and/or nutritional substances, procedures, processes, and/or practices of interest for use in a health regimen or regimens. The vendor interface device 114 may be a keyboard, mouse, trackball, monitor, microphone and speakers, and/or other interface device or devices for a human to interface with the vendor logic 116 of computer 118. The vendor logic 116 may include at least a portion of the hardware/software/firmware of the computer 118. The vendor 112 may use the computer 118 to provide information and channels, making the vendor 112 available to provide pharmaceutical, nutraceutical, veterinary, dietary, and/or nutritional substance, procedure, processes, and/or practices of interest, via another computer or computers represented by the network 110, to, among others, the end-user 102.

Publisher 120 is a person and/or persons and/or entity and/or entities that may supply information about pharmaceutical, nutraceutical, veterinary, dietary, and/or nutritional substances procedures, processes, and/or practices of interest for use in a health regimen or regimens, and/or about authorities having expertise or claimed expertise regarding pharmaceutical, nutraceutical, veterinary, dietary, and/or nutritional substances procedures, processes, and/or practices of interest for use in a health regimen or regimens. The publisher interface device 122 may be a keyboard, mouse, trackball, monitor, microphone and speakers, and/or other interface device or devices for a human to interface with the publisher logic 124 of computer 126. The publisher logic 124 may include at least a portion of the hardware/software/firmware of the computer 126. The publisher 120 may use the computer 126 to provide such information about pharmaceutical, nutraceutical, veterinary, dietary, and/or nutritional substance, procedure, processes, and/or practices of interest, via another computer or computers represented by the network 110, to, among others, the end-user 102. The publisher 120 represents a wide variety of information providers, including but not limited to magazine publishers, book publishers, website maintainers, weblog proprietors, experts, research organizations, and users of the pharmaceutical, nutraceutical, veterinary, dietary, and/or nutritional substances procedures, processes, and/or practices of interest.

End-users 102, vendors 112, and publishers 120 are not mutually exclusive categories. One person, group of persons, entity, or group of entities may be categorized as an end-user 102, vendor 112, and/or publisher 120 simultaneously or at different times. End-users 102, vendors 112, and publishers 120 are exemplary parties and do not represent all users. Exemplary descriptions including the end-user 102 are not limiting and do not preclude use of an embodiment by vendors 112 and/or publishers 120.

Figure 2:
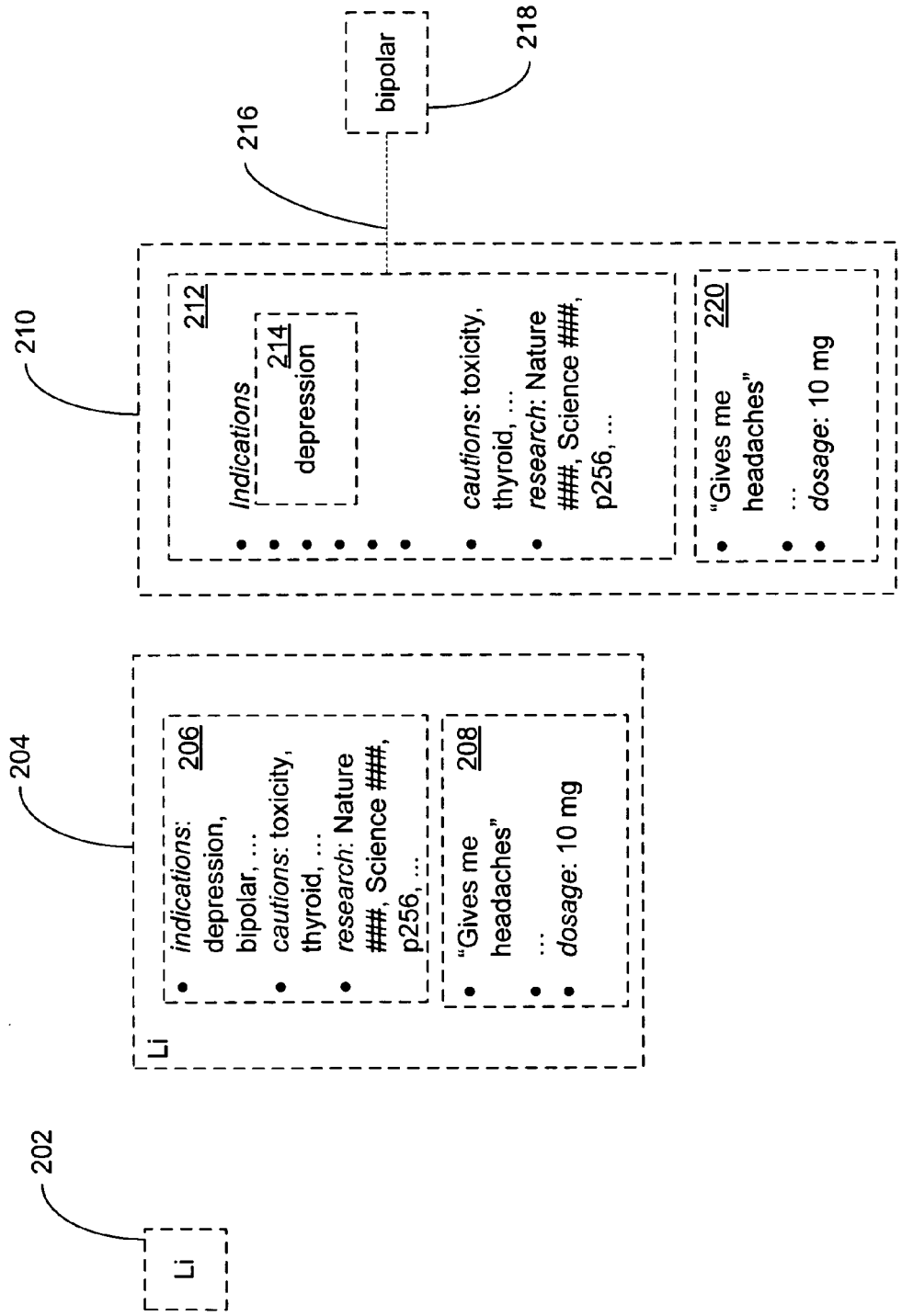
FIG. 2 depicts alternative exemplary embodiments.

FIG. 2 depicts alternative exemplary embodiments of a data entity, including depiction of alternative exemplary embodiments of health regimen data entities associated with some amount of additional information. This additional information may include but is not limited to an item of associative information, e.g., a linkage or a resolvable reference, to one or more other health regimen data entities in the data structure/data structures (e.g., which may be distributed data structures), e.g., a pointer, identifier, and/or a link. In FIG. 2 and the other figures, items of associative data are depicted by lines and/or arrows between health regimen data entities, or are implicit of the relationship between a nesting health regimen data entity and any health regimen data entity nested within or at any depth; such implicit items of associative data are shown by the illustrated nesting. The additional information may also include but is not limited to substantive information, e.g., where the health regimen data entity includes the identity of a substance and the additional information describes a potential use or specifies a dosage. Here health regimen data entity 202 includes an identifier for the element lithium (Li). The health regimen data entity 204 illustrates an alternative exemplary embodiment of the health regimen data entity 202. The end-user 102 may select the health regimen data entity 202 to access additional information that is included in association with the health regimen data entity 202. The additional information may be organized in some defined way, as illustrated in organizational structure 206, or unorganized as in collection 208. The health regimen data entity 210 shows another alternative exemplary embodiment of the health regimen data entity 202. Here the additional information is illustrated as being included in an organizational structure 212. One of the items of additional information associated with the organizational structure 212 is depicted as another health regimen data entity 214 "nested" within health regimen data entity 212. Another of the items of additional information associated with the health regimen data entity 212 is linked by an item of associative information 216 to another health regimen data entity 218. Organizational principles such as those illustrated by the relationship between health regimen data entity 212 and health regimen data entity 214, and by the relationship between health regimen data entity 212, item of associative information 216, and health regimen data entity 218, may be replicated at any level of an organizational structure, or in an unorganized collection such as collection 220. It is to be understood that in substantially all examples referring to "an identifier for lithium" herein, analogous examples utilizing the alternatives such as those from FIG. 2, will be recognized by those of skill in the art. Such examples are not expressly set forth herein for the sake of clarity.

Figure 3:
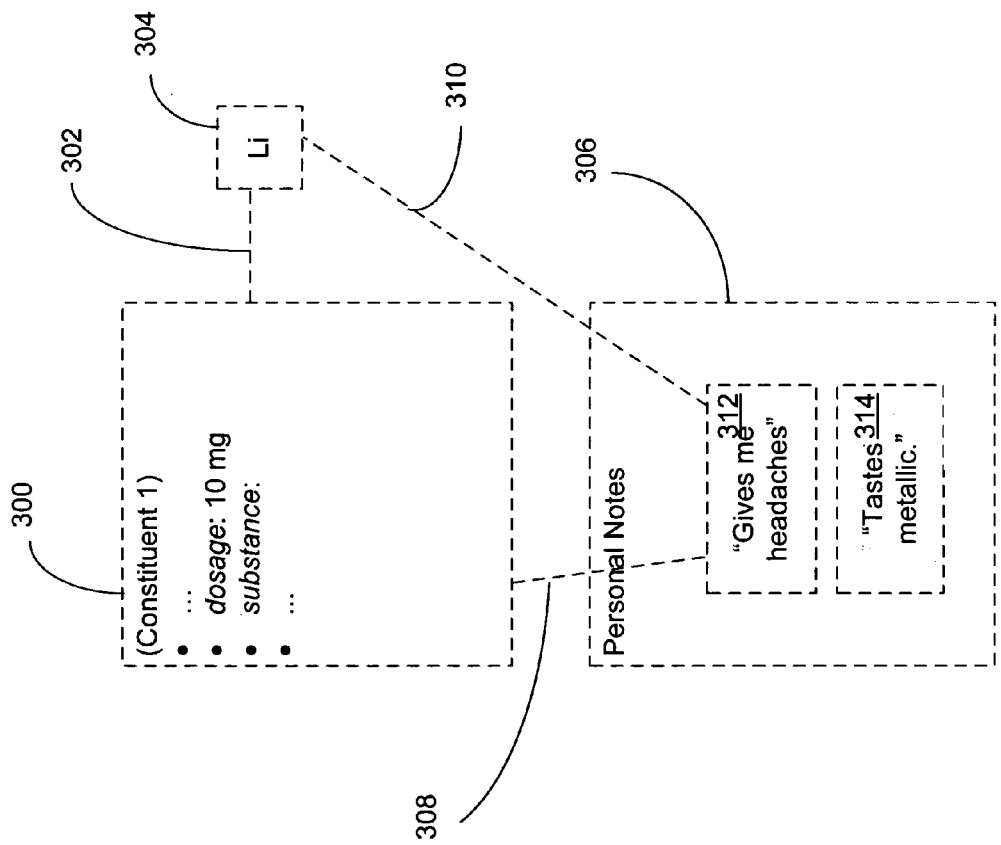
FIG. 3 illustrates alternative exemplary embodiments.

FIG. 3 illustrates an alternative exemplary embodiment of a health regimen data entity. Depicted is nesting health regimen data entity 300, which includes additional information relevant in the context of the nesting health regimen data entity 300, here, "constituent 1." The identity of constituent 1 is not nested within nesting health regimen data entity, but an item of associative data 302 links to a health regimen data entity 304 identifying lithium ("Li"). Also illustrated is a health regimen data entity 306 having additional information detailing personal notes from users of constituent 1. Shown are nested health regimen data entities 312 and 314. The health regimen data entity 312 is linked to the nesting health regimen data entity 300 by an item of associative data 308 and to the health regimen data entity 304 by an item of associative data 310.

Figure 4:
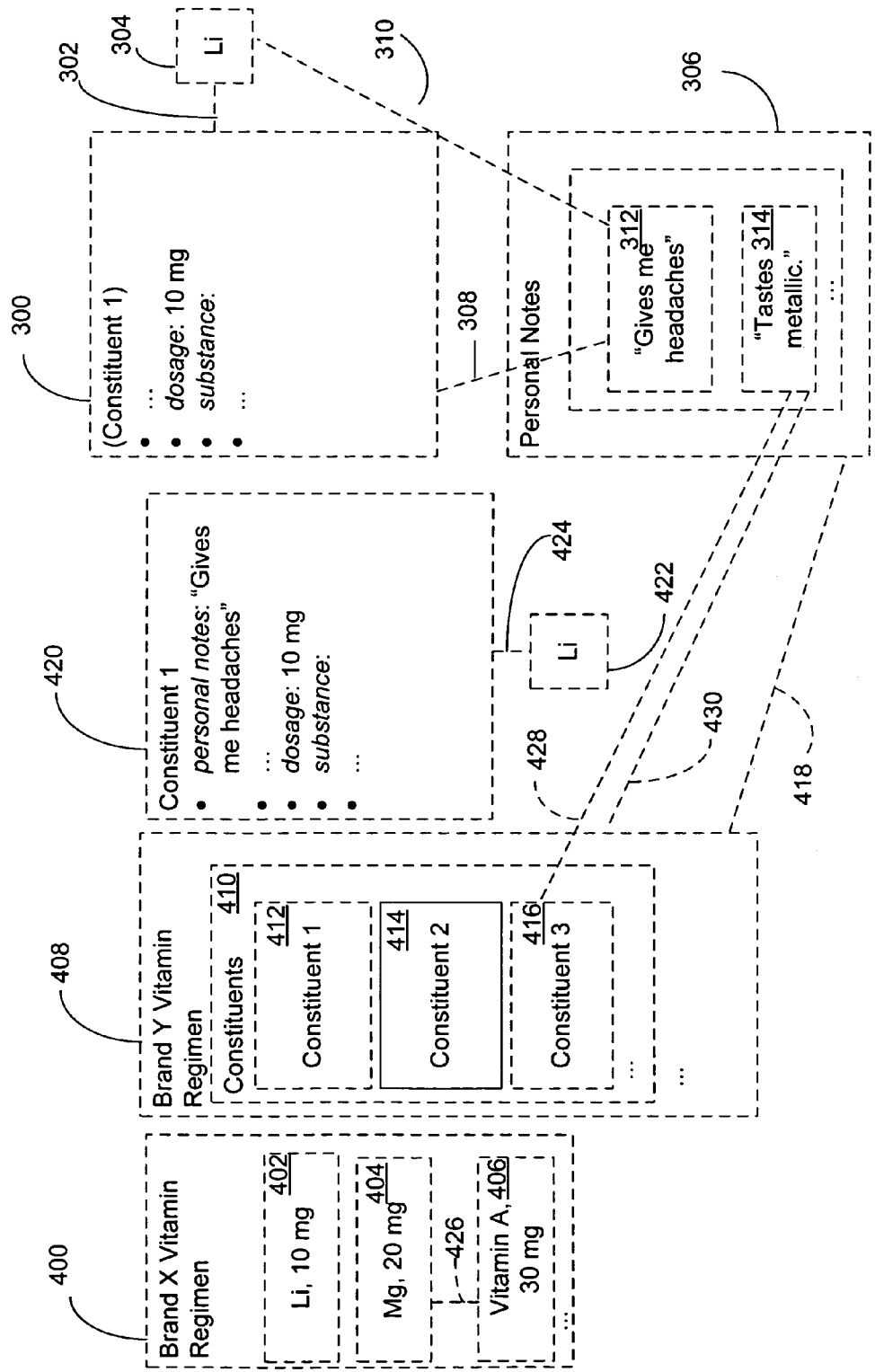
FIG. 4 illustrates alternative exemplary embodiments.

FIG. 4 illustrates a number of alternative exemplary health regimen data entities organized in the data structure according to different organizational schemes. Shown is nesting health regimen data entity 400, including three nested health regimen data entities 402, 404, and 406, for three components of a "Brand X" vitamin regimen. Depicted is nesting health regimen data entity 408, including a nested and nesting health regimen data entity 410. Nested and nesting health regimen data entity 410 includes nested health regimen data entities 412, 414, and 416, components of a "Brand Y" vitamin regimen. Illustrated is nesting health regimen data entity 408 associated with health regimen data entity 306 with an item of associative data 418, linking the personal notes of health regimen data entity 306 with the "Brand Y" vitamin regimen of nesting health regimen data entity 408. Illustrated is health regimen data entity 420, pertaining to "constituent 1," including additional information about personal notes, dosage, and substances. The health regimen data entity 420 is shown linked to health regimen data entity 422, identifying Lithium, by an item of associative data 424. The health regimen data entity 406 is shown linked to another health regimen data entity 404 by an item of associative data 426. The health regimen data entity 314 is shown linked to the health regimen data entity 416 by an item of associative data 428. The health regimen data entity 314 is also shown linked to health regimen data entity 416 by an item of associative data 430.

The nesting as illustrated in FIGS. 2, 3, and 4 is accomplished with items of associative information that are associated with either the nesting health regimen data entity or with one or more of the illustrated nested health regimen data entities. The nesting health regimen data entity might represent, e.g., the name of a vitamin supplement, and the nested health regimen data entities might represent, e.g., five constituent supplements comprised by the named vitamin supplement. In another example, the nesting health regimen data entities might represent identifiers of taxonomic classifications to which the constituent belongs, such as chemical classes (such as water soluble or fat soluble vitamins), classes of effect or action (such as beta-blockers, neurotransmitters, or strength enhancers).

A health regimen data entity may be associated with another health regimen data entity in a variety of ways. The first health regimen data entity may be associated with the second health regimen data entity with an item of associative information associated with one or the other or both. The first health regimen data entity may be associated with the second health regimen data entity as well as with additional health regimen data entities simultaneously. The multiply-referenced health regimen data entity may actually be multiple health regimen data entities in the data structure, or it may be a single health regimen data entity with multiple items of associative information used to reference it.

Figure 5:
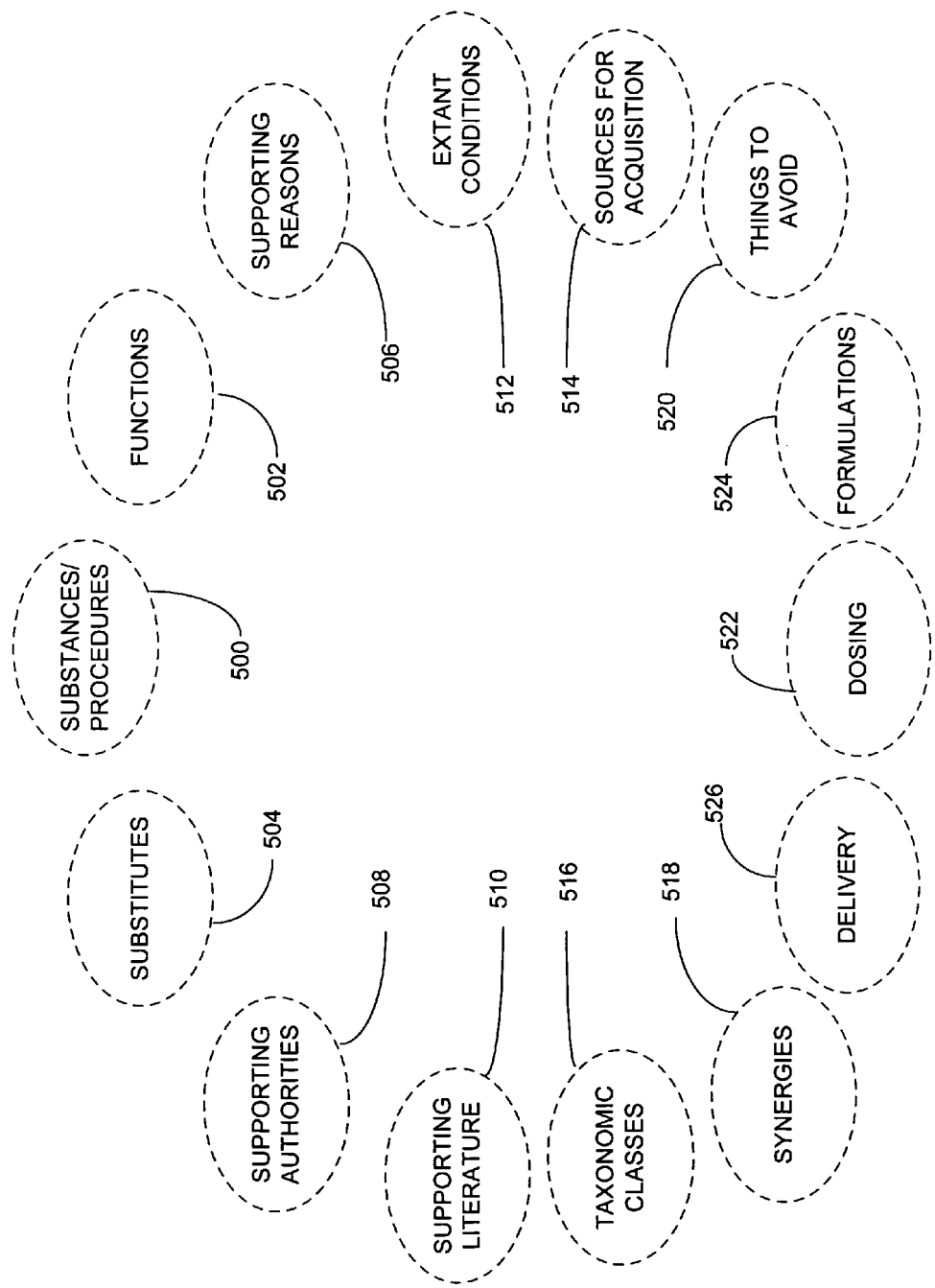
FIG. 5 depicts alternative exemplary aspects of embodiments.

FIG. 5 depicts a number of alternative exemplary topics which may be used in the data structure. The identity of a topic may be represented by a health regimen data entity, and association with a topic accomplished by use of an item of associative information. At least some health regimen data entities may be associated with topics of interest to the end-user 102 to provide a schema with which to begin use of the information in the data structure. Each of the topics is exemplary, but they serve to illustrate a particular application which is not limiting. An end-user 102 may start retrieving data from the data structure by starting with any topic in the data structure. Each item of data stored in association with each topic may have associated using an item of associative information with another item of data associated with the same topic or with another topic, such that an end-user 102 starting with an item of data in a particular topic, e.g., a name of Substance A under the topic Substances/Procedures, may choose to retrieve another item of data associated with Substance A via a an item of associative information to a health regimen data entity associated with another topic, e.g., a function of Substance A, relief of joint pain, associated with the topic Functions. The end-user 102 may continue by selecting an item of data associated with a third topic, e.g., a Substitute B for Substance A for the relief of joint pain, associated with the topic Substitutes. The end-user 102 may continue in this fashion through all of the data items in the topics in the data structure associated via items of associative information to the selections of the end-user 102.

Although shown for clarity in FIG. 5 as discrete topics, generally, topics may be associated with or even be composed of other topics, and a given topic or reference to that topic may be associated with another discrete topic.

The topic 500, "Substances/Procedures," may include common, generic, commercial, and/or trade names and/or descriptions for pharmaceutical, nutraceutical, veterinary, dietary, and/or nutritional substances, procedures, processes, and/or practices of interest to an end-user 102.

The topic 502, "Functions," may include one or more descriptions of functions for which the substances of the topic 500, "Substances/Procedures" may be used by humans in connection with human physical and/or mental conditions, and/or veterinary purposes.

The topic 504, "Substitutes," may include common, generic, commercial, and/or trade names and/or descriptions for pharmaceutical, nutraceutical, veterinary, dietary, and/or nutritional substances, procedures, processes, and/or practices of interest to an end-user 102, which may be substituted to perform functions associated with the topic 502, "Functions."

The topic 506 "Supporting Reasons," may include explanations for the functionality of the substances/procedures and substitutes included in the topics 500, "Substances/Procedures" and 504, "Substitutes."

The topic 508, "Supporting Authorities," may include the identities and credentials of people and/or entities which endorse the use of substances/procedures and substitutes for various functions. The supporting authorities may include medical and/or veterinary professionals and/or experts of various kinds ("gurus"), and/or manufacturers and/or distributors of substances/procedures and substitutes. The topic 508, "Supporting Authorities," may also include testimonials and/or reports and/or anecdotal evidence from other end-users 102, and may include descriptors of factors associated with those end-users 102 to permit manual or automatic correlation of their experience with the potential experience of the end-user 102 consulting the data structure.

The topic 510, "Supporting Literature," may include references to published articles and/or other publicly available information, by citation and/or hyperlink and/or other reference means, e.g., referred journal articles and/or magazine articles and/or website articles, pertaining to the functionality of substances/procedures and substitutes.

The topic 512, "Extant Conditions," may include one or more selections of descriptors that describe internal physical and/or mental and/or environmental and/or spiritual and/or metaphysical factors of interest to the end-user 102 and of possible relevance to the functionality of substances/procedures and substitutes. Internal physical factors may include body temperature, medical condition, genetic information, and/or substances/procedures or substitutes ingested or to be ingested. Mental factors may include a diagnosed mental condition, a subjective mental state, genetic information, and/or substances/procedures or substitutes ingested or to be ingested. Environmental factors may include external temperature, humidity, barometric pressure, ambient light intensity, and, for some, the date, the positions of the planets, geographical factors such as those relevant to feng shui, and/or other factors relevant to disciplines, traditions, and arts considered relevant by the end-user 102 and/or by a contributor of information to the data structure and/or by a third-party authority such as an expert or a source for acquisition. Where feasible, values for external factors may be provided to the data structure in the form of health regimen data entities representing the output of instrumentation, e.g., weather instrumentation or medical instrumentation.

The topic 514, "Sources for Acquisition," may include identities of, contact information for, and/or channels of communication with persons and/or entities from which substances/procedures or substitutes may be purchased or otherwise acquired by the end-user 102. Such sources may pay to be included in the data structure in association with this topic.

The topic 516, "Taxonomic Classes," may include various categories with which substances/procedures and/or substitutes may be associated, e.g. acids, derivatives from X, etc.

The topic 518, "Synergies," may include substances/procedures, substitutes, activities, and/or extant conditions that, acting together with a substance or substitute, enhance the functionality of the substance or substitute; favorably change the amount or timing or the substance or substitute needed for the desired functionality; and/or provide one or more additional desirable functionalities beyond those associated with the substance or substitute taken by itself.

The topic 520, "Things to Avoid," may include substances/procedures, substitutes, activities, and/or extant conditions that, acting together with a substance or substitute, detracts from the functionality of the substance or substitute; unfavorably changes the amount or timing or the substance or substitute needed for the desired functionality; and/or provides one or more additional undesirable functionalities beyond those associated with the substance or substitute taken by itself.

The topic 522, "Dosing," may include information pertaining to the mode, amount, conditions, and/or timing of the delivery of a substance or substitute to achieve the desired functionality, along with synergies and things to avoid, e.g., 200 mg capsules of Substance A, taken twice daily when sunny and thrice daily when cloudy or raining; or once daily under any conditions no matter the weather, and never to be taken when Substance B has been taken within 24 hours. Beyond that simple example, the topic 522, "Dosing," may include a procedure for determining an amount and/or timing for the substance to be taken, rather than a simple fixed value, along with factors that give the end-user 102 options based on probabilities and other factors such as extant conditions, e.g., when the weather is hot and the end-user 102 is feeling irritable, an option to reduce a lithium dose by one pill per day, and if that does not work, by two pills per day, but never by more than two pills per day. These options and alternatives to them may also be accessed by associations with other health regimen data entities, including, e.g., hot days, lithium, and/or irritability.

The topic 524, "Formulations," may include information pertaining to the constituents of a substance, including but not limited to the identities of the constituents, the amounts of the constituents present per unit of the substance, and/or the method(s) for combining the constituents to form the substance. In particular, the amounts of the constituents may be represented by listing the amounts numerically, and/or by a formula or formulas from which each constituent amount may be derived either by the end-user 102 or by computational resources associated with the data structure. In an embodiment, the end-user 102 may follow items of associative information to health regimen data entities and/or additional information that provide information on the sources of formulary information, e.g., an article on an experiment, or on the instruments that provided the formulary information, e.g., an indication of what the underlying methodology of selection is at least partially based upon (e.g., animal studies, human studies, in silico studies, speculation, anecdotal information, historical accounts, traditions, cultural practices, native practices, etc.

The topic 526, "Delivery," may include information on methods of delivery, e.g., orally by capsule, orally by liquid dose, epidermally by patch, injection by syringe, and/or internally by timed release from an implanted reservoir, and on formulations, dose sizes, and dose timings associated with various delivery methods.

Figure 6:
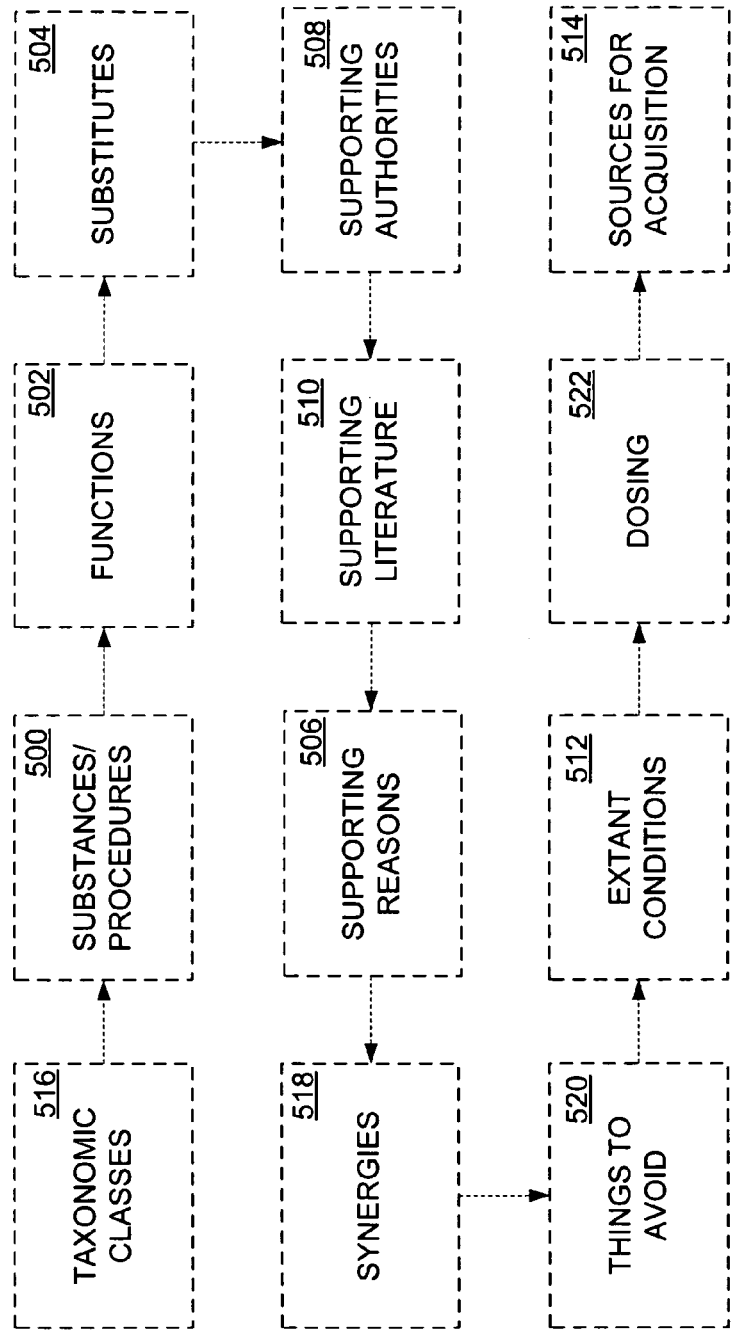
FIG. 6 depicts an exemplary view of aspects of an embodiment.

FIG. 6 depicts an exemplary way to view a pathway of an end-user 102 through data in the data structure. The end-user 102 in this exemplary view starts with taxonomic classes, e.g. vitamins, selects a vitamin, e.g., Vitamin X, and selects an associated function, e.g., increased energy. The end-user 102 finds a substitute for Vitamin X for increasing energy, e.g., Substance Y, refers to supporting authorities, e.g., a particular columnist for a magazine, supporting literature, e.g., an article in JAMA, and supporting reasons, e.g., a web-based explanation for the effects of Substance Y on energy. From there, the end-user 102 calls up information on synergies, e.g., Substance Z as being synergistic with Substance Y, providing increased memory when they are used together, along with things to avoid, e.g., not using Substance W in conjunction with Substance X because such conjunctive use causes impotence. The end-user 102 may consult "Extant Conditions" to learn that Substance X has an increased effect at lower altitudes and/or when certain planets are in a particular astrological configuration. The end-user 102 may consult the "Dosing" topic for information on dosing under various conditions, and she may peruse sources for acquisition to select a mode of purchase, to conclude the purchase, and to arrange for delivery.

Figure 7:
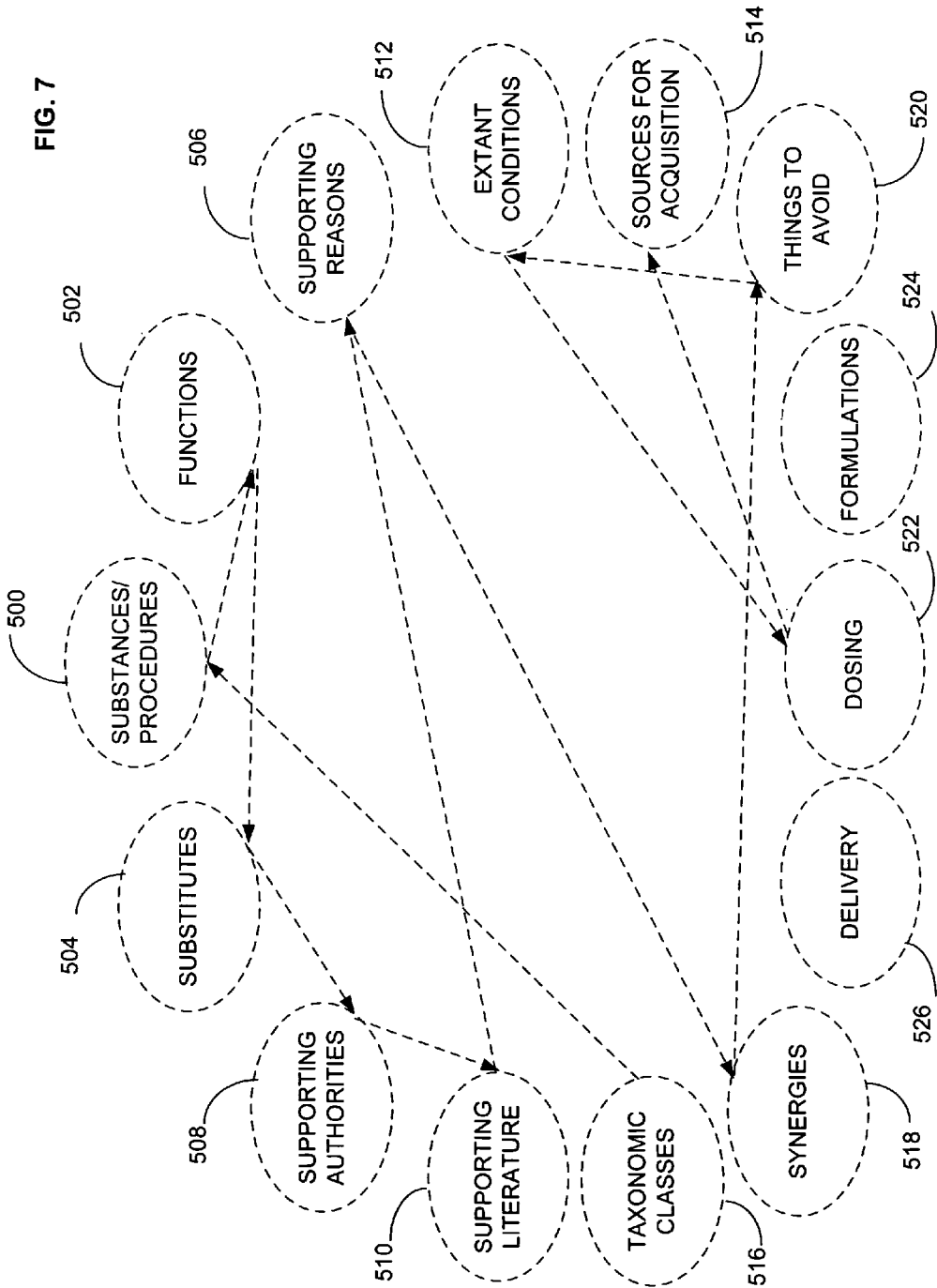
FIG. 7 depicts an alternative exemplary view of the aspects of the embodiment depicted in FIG. 6.

FIG. 7 depicts an alternative exemplary way to view the pathway of an end-user 102 through data in the data structure depicted in FIG. 6, using as a template the depiction of FIG. 5.

Figure 8:
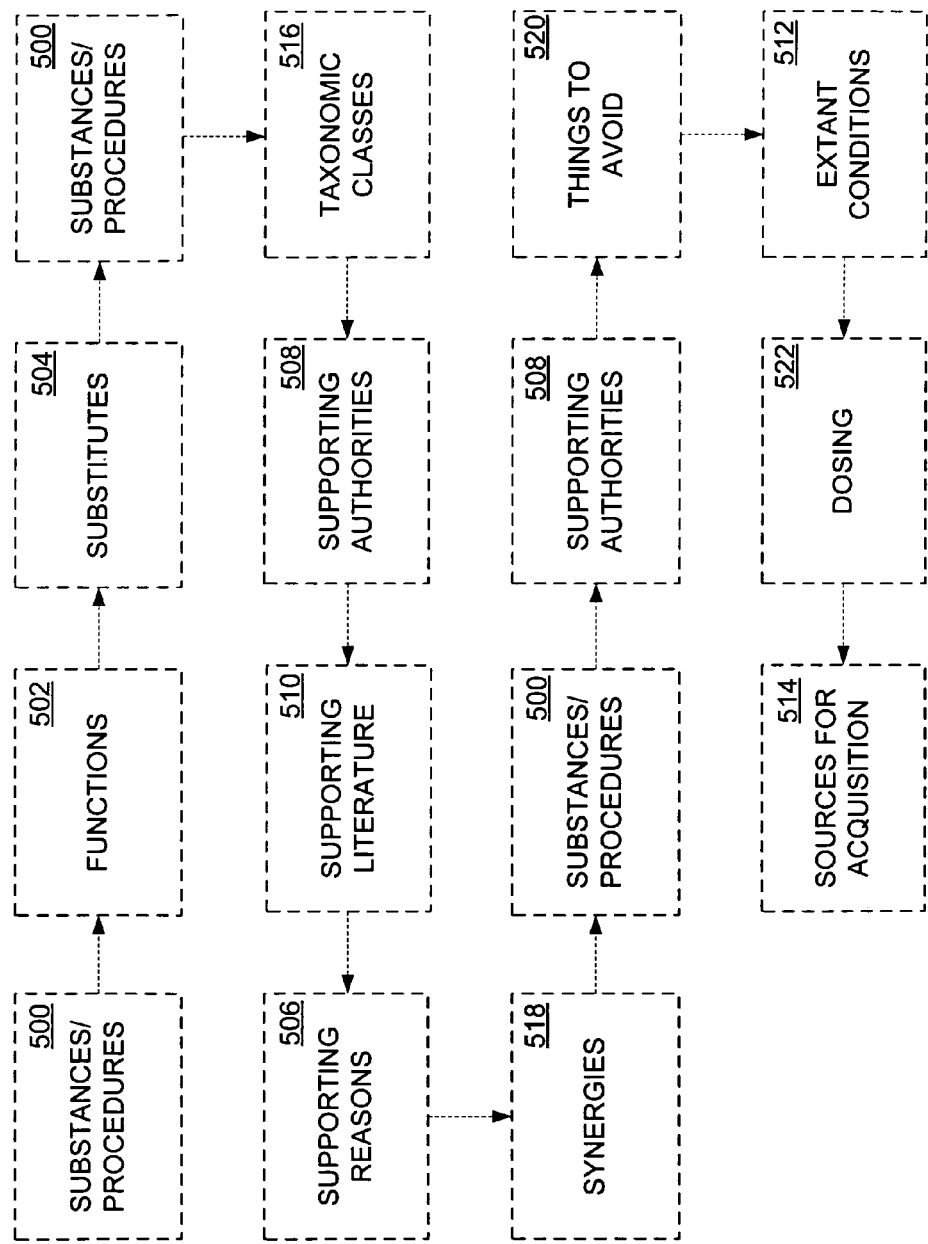
FIG. 8 depicts an exemplary view of aspects of an embodiment.

FIG. 8 depicts an exemplary view of the pathway of an end-user 102 through data in the data structure. The end-user 102 starts with a substance, e.g., Substance M, and looks up functions for Substance M, e.g., protection against cancer. The end-user 102 then looks up substitutes for Substance M for protection against cancer, e.g., Substance N. The end-user 102 then becomes interested in Substance N for other purposes. Going back to the topic "Substances/Procedures" to learn about Substance N, the end-user 102 learns that Substance N is a member of a particular taxonomic class, e.g. acids. The end-user 102 reassures himself of the efficacy of Substance N for some other purpose, e.g., prevention of hair loss, by consulting a supporting authority, e.g., a famous cancer researcher, supporting literature, e.g., a *Scientific American* article, and supporting reasons, e.g., a published explanation of why Substance N prevents hair loss. The end-user 102 retrieves information on synergies from the use of Substance N and Substance 0, e.g., enhanced prevention of hair loss and fresher breath, and on things to avoid, e.g., the use of Substance N with, e.g., Substance P, which would lead to decreased efficacy for hair loss and extensive skin rashes. The end-user 102 calls up the effects of extant conditions on the use of Substance N, e.g., amplification of any already-present schizophrenia when certain planets are in a particular astrological configuration. The end-user 102 finishes by retrieving dosing information and proceeding to purchase through a source for acquisition.

Figure 9:
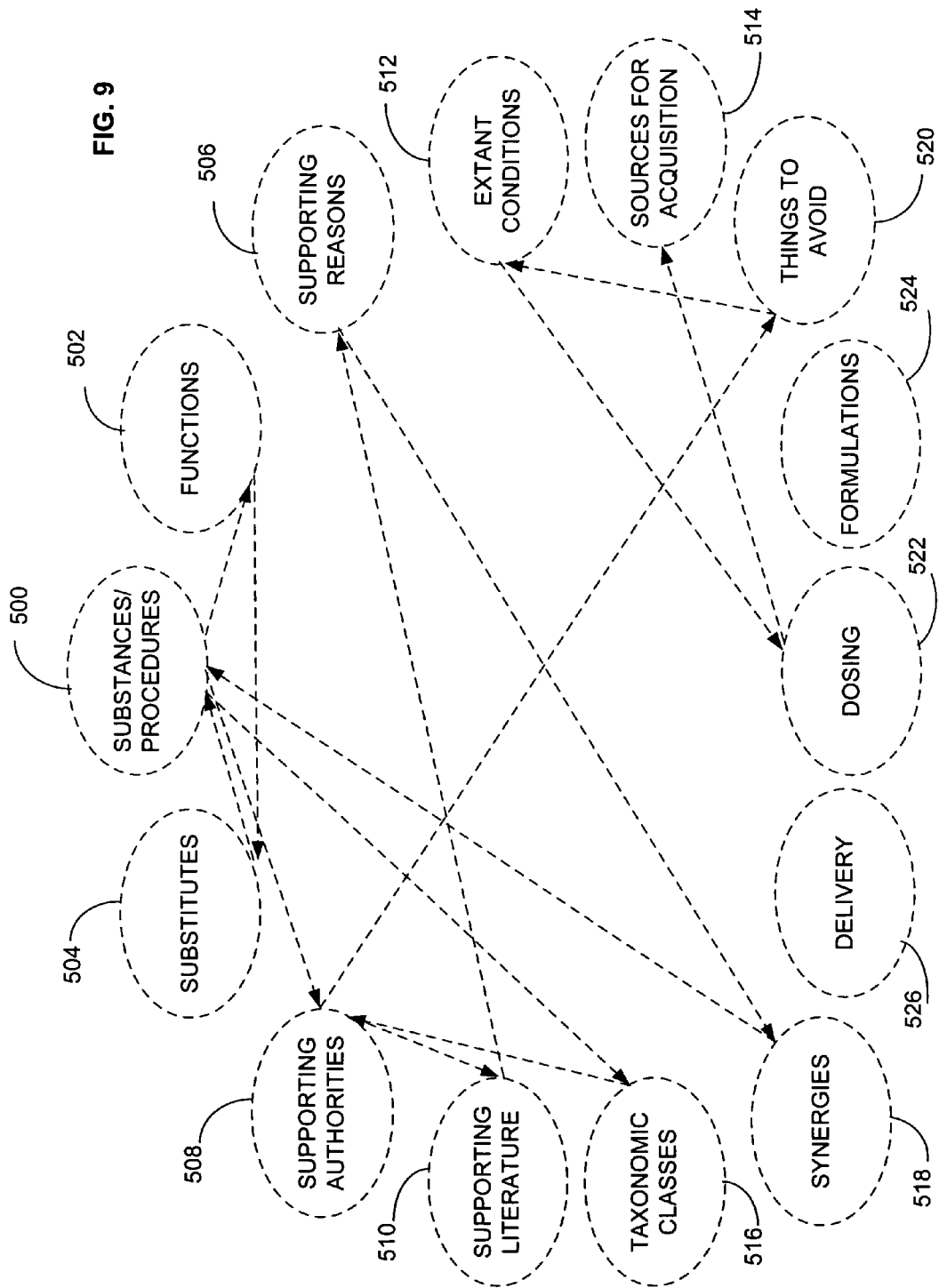
FIG. 9 depicts an alternative exemplary view of the aspects of the embodiment depicted in FIG. 8.

FIG. 9 depicts an alternative exemplary way to view the pathway of an end-user 102 through data in the data structure depicted in FIG. 8, using as a template the depiction of FIG. 5.

Figure 10:
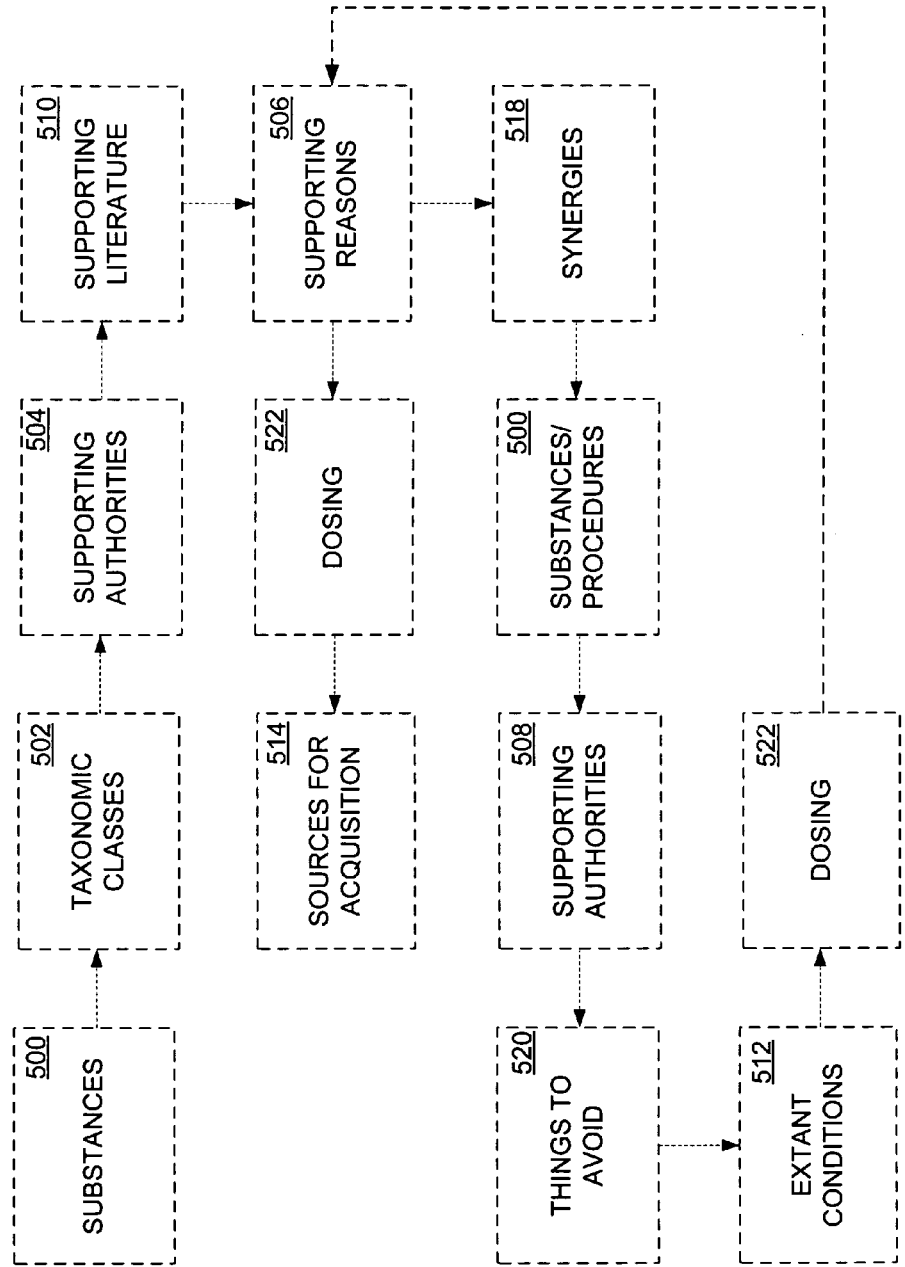
FIG. 10 depicts an exemplary view of aspects of an embodiment.

FIG. 10 depicts an exemplary way to view a branched pathway of an end-user 102 through data in the data structure. The end-user starts with a substance, e.g., Substance P, and looks up taxonomic classes associated with for Substance P, e.g., water soluble vitamins. The end-user 102 then looks up supporting authorities for the use of water soluble vitamins for protection against cancer, such as a columnist in a well-known health magazine, and moves on to supporting literature, e.g., articles in reference journals, and supporting reasons, e.g., explanations of the functionality of water soluble vitamins for prevention of cancer. At this point, the end-user 102 remembers that a friend had been asking about the use of water soluble vitamins for other purposes, such as prevention of hair loss, especially in combination with certain procedures for their use. Leaving aside his original search, the end-user 102 takes up his friend's question and looks up synergies with regard to water soluble vitamins. After perusing synergies, he selects a procedure, e.g., taking a particular water soluble vitamin in conjunction with a food such as a particular fruit. He looks up supporting authorities for the efficacy of the water soluble vitamin in conjunction with the fruit for preventing hair loss, e.g., a medical society. He then checks for things to avoid, such as the use of a second vitamin that would reduce the effectiveness of the first vitamin and the fruit, and extant conditions, such as humidity, which might affect the usefulness of the water soluble vitamin. Finally, he looks at the appropriate dosing for the water soluble vitamin. Having investigated his friend's question, he returns to his original search. He had been looking up supporting reasons for the use of water soluble vitamins to prevent cancer. He resumes his research at that point and moves on to investigate appropriate dosing. Finally, he moves to sources for acquisition of the Substance P.

Figure 11:
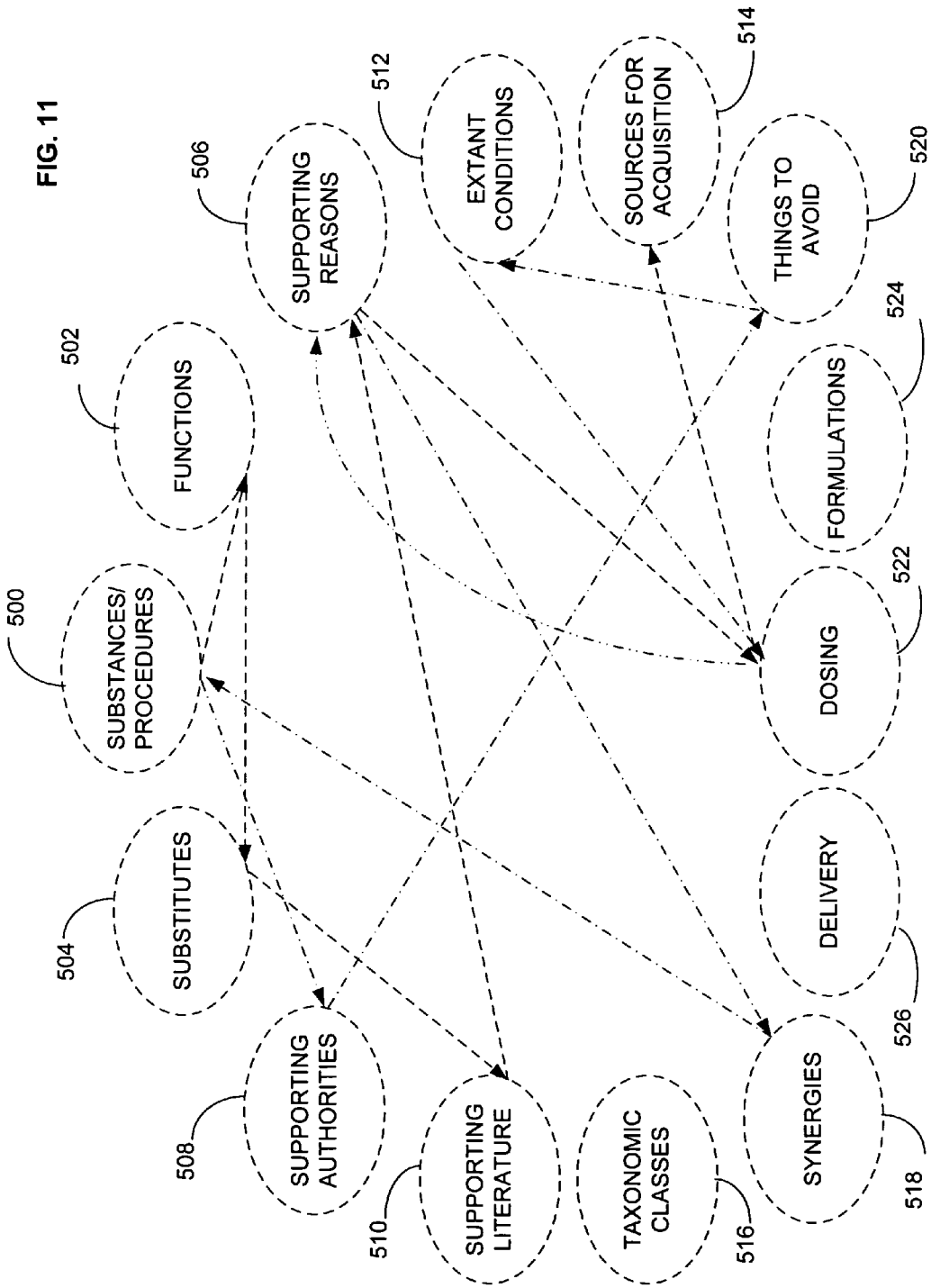
FIG. 11 depicts an alternative exemplary view of aspects of the embodiment depicted in FIG. 10.

FIG. 11 depicts an alternative exemplary way to view the pathway of an end-user 102 through data in the data structure depicted in FIG. 10, using as a template the depiction of FIG. 5.

The end-user 102 may search the data structure for patterns, finding correlations between health regimen data entities that would otherwise not be discoverable or that would be very difficult to discover. For example, the end-user 102 may search for effects of Substance A on skin rashes in conditions of high humidity, searching, among other health regimen data entities, those including anecdotal evidence from users of Substance A in high humidity, where the users of Substance A also had skin rashes and reported apparent effects of Substance A on those rashes. Such searches for correlations may include information and observations added to the data structure by all or any of the end-users 102, vendors 108, and/or publishers 112 using the data structure. Such searches may be used to test hypotheses about the efficacy and safety of pharmaceutical, nutraceutical, veterinary, dietary, and/or nutritional substances, procedures, processes, and/or practices of interest.

As mentioned above, end-users 102 may add health regimen data entities to the data structure to report experiences with the use of substances/procedures. For example, an end-user 102 may integrate a report of an experience, e.g., partial success with the use of Substance B for reduction of hair loss in low-humidity conditions but little success in conditions of high-humidity, by selecting pre-existing health regimen data entities with which to associate new health regimen data entities that represent relevant elements of his report, and/or by associating new health regimen data entities that represent relevant elements of his report with pre-existing annotations to pre-existing health regimen data entities added by other end-users 102 with similar reports. An end-user 102 may also add health regimen data entities representing the results of correlative searches such as those described above, e.g., by adding health regimen data entities representing the results of such a search and associating them with pre-existing health regimen data entities associated with, e.g., a Substance C used to alleviate heartburn in connection with particular dietary conditions.

In using the data structure, the end-user 102 may impose his own schema on the information searched and on the output of the search. The end-user 102 may explicitly include or exclude for search purposes health regimen data entities representing factors such as weather information or astrological information. He may include or exclude for search results reporting purposes various complexities, e.g., including tables of correlations for further study, but excluding such information and including only lists of ingredients and instructions for purposes of making a particular substance for use or lists of dosages to serve as input into medical dispensing devices, either indirectly through human input to devices or automatically through direct input of dosage information to devices.

Figure 12:
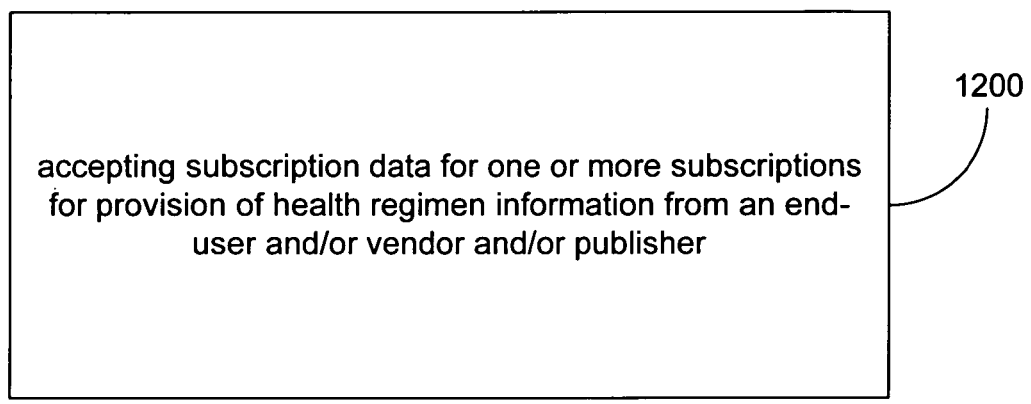
FIG. 12 depicts a high-level logic flowchart of an operational process.

FIG. 12 depicts a high-level logic flowchart of an operational process. Operation 1200 shows accepting subscription data for one or more subscriptions for provision of health regimen information from an end-user and/or vendor and/or publisher (e.g., accepting subscription data for one or more subscriptions for provision of health regimen information from an end-user and/or vendor and/or publisher, via an end-user interface device 104 and/or vendor interface device 114 and/or publisher interface device 112 and end-user logic 106 and/or vendor logic 116 and/or publisher logic 124, such as the period of time for which a subscription is to be active, where the health regimen information is stored on computer 108 and/or computer 118 and/or computer 126).

Figure 13:
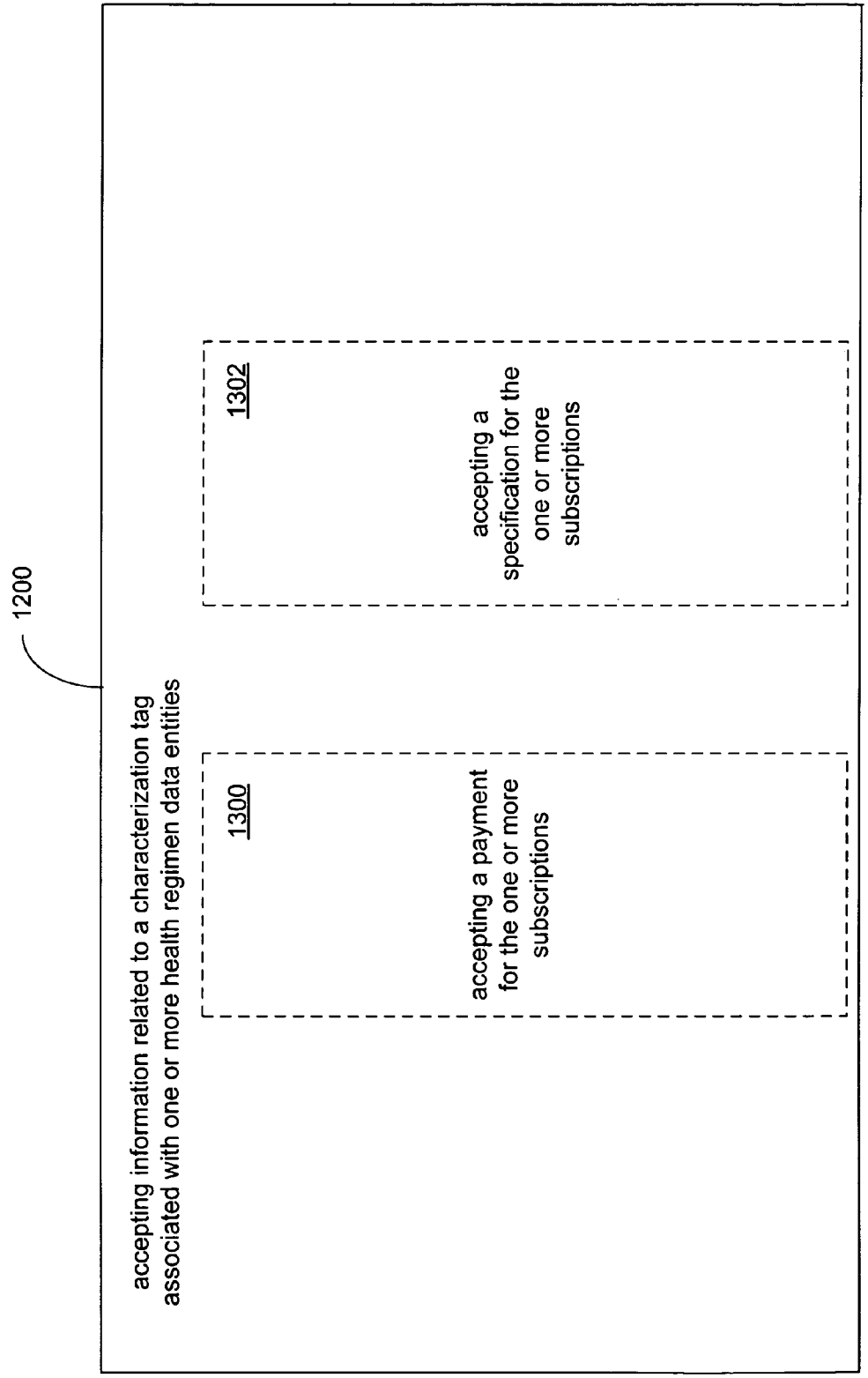
FIG. 13 shows several alternative implementations of the high-level logic flowchart of FIG. 12.

FIG. 13 shows several alternative implementations of the high-level logic flowchart of FIG. 12. Operation 1200—accepting subscription data for one or more subscriptions for provision of health regimen information from an end-user and/or vendor and/or publisher—may include one or more of the following operations: 1300 and/or 1302. Operation 1300 depicts accepting a payment for the one or more subscriptions (e.g., accepting a payment for the one or more subscriptions, via an end-user interface device 104 and/or vendor interface device 114 and/or publisher interface device 112 and end-user logic 106 and/or vendor logic 116 and/or publisher logic 124, such as accepting a credit card number and an amount to be charged to the credit card account, where the health regimen information is stored on computer 108 and/or computer 118 and/or computer 126). Operation 1302 shows accepting a specification for the one or more subscriptions (e.g., accepting a specification for the one or more subscriptions, via an end-user interface device 104 and/or vendor interface device 114 and/or publisher interface device 112 and end-user logic 106 and/or vendor logic 116 and/or publisher logic 124, such as accepting an identification of the health regimen information desired by the subscriber, where the health regimen information is stored on computer 108 and/or computer 118 and/or computer 126).

Figure 14:
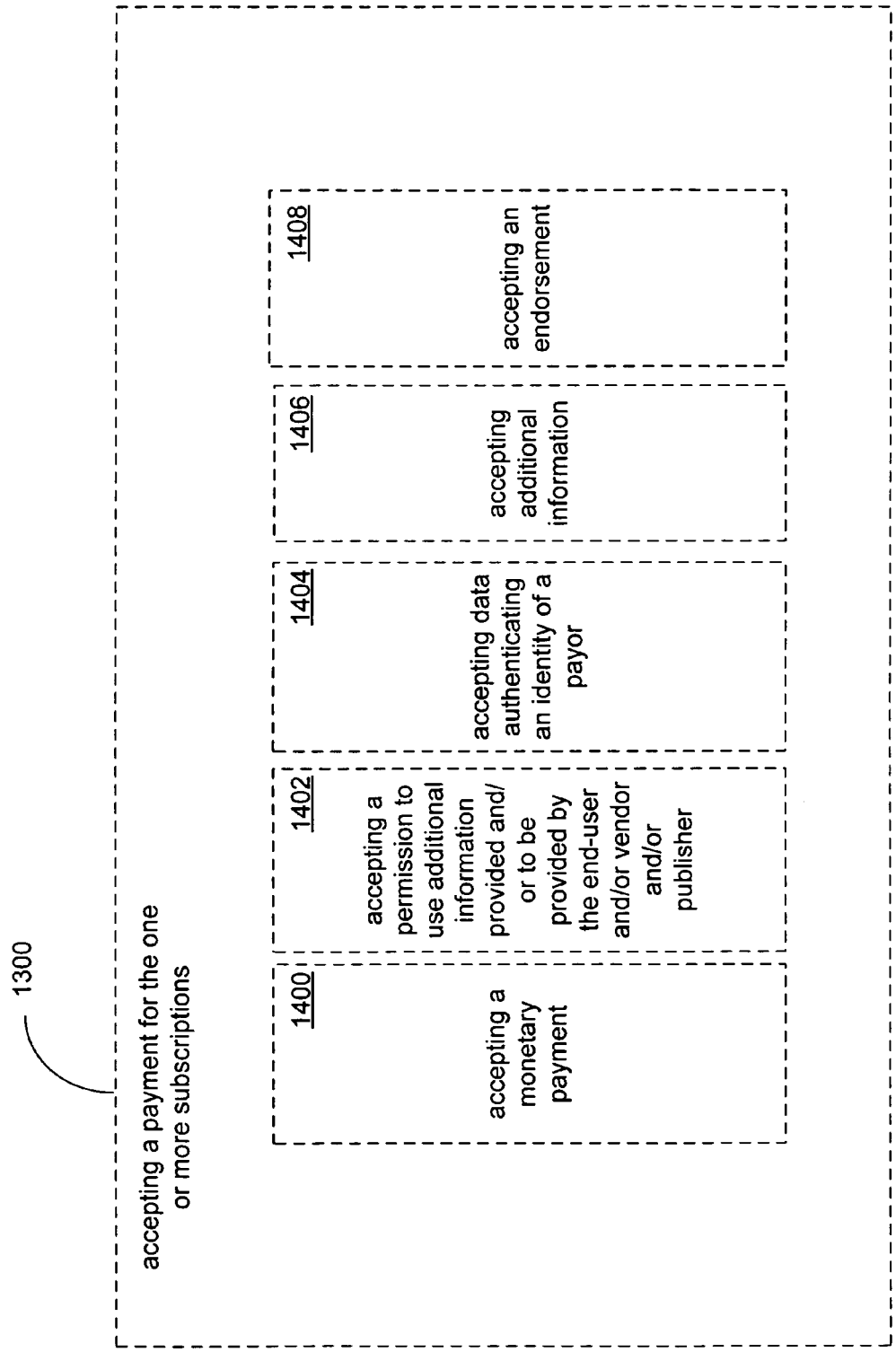
FIG. 14 shows several alternative implementations of the high-level logic flowchart of FIG. 13.

FIG. 14 shows several alternative implementations of the high-level logic flowchart of FIG. 13. Operation 1300—accepting a payment for the one or more subscriptions—may include one or more of the following operations: 1400, 1402, 1404, 1406, and/or 1408. Operation 1400 illustrates accepting a monetary payment (e.g., accepting a monetary payment, via an end-user interface device 104 and/or vendor interface device 114 and/or publisher interface device 112 and end-user logic 106 and/or vendor logic 116 and/or publisher logic 124, such as accepting a credit card number and an amount to be charged to the credit card account, where the health regimen information is stored on computer 108 and/or computer 118 and/or computer 126). Operation 1402 depicts accepting a permission to use additional information provided and/or to be provided by the end-user and/or vendor and/or publisher (e.g., accepting a permission to use additional information provided and/or to be provided by the end-user and/or vendor and/or publisher, via an end-user interface device 104 and/or vendor interface device 114 and/or publisher interface device 112 and end-user logic 106 and/or vendor logic 116 and/or publisher logic 124, such as accepting a permission to use information contributed and/or to be contributed by the subscriber in partial exchange for the desired subscription, where the health regimen information is stored on computer 108 and/or computer 118 and/or computer 126). Operation 1404 illustrates accepting data authenticating an identity of a payor (e.g., accepting data authenticating an identity of a payor, via an end-user interface device 104 and/or vendor interface device 114 and/or publisher interface device 112 and end-user logic 106 and/or vendor logic 116 and/or publisher logic 124, such as accepting a user name and/or password from the subscriber, where the health regimen information is stored on computer 108 and/or computer 118 and/or computer 126). Operation 1406 depicts accepting additional information (e.g., accepting additional information, via an end-user interface device 104 and/or vendor interface device 114 and/or publisher interface device 112 and end-user logic 106 and/or vendor logic 116 and/or publisher logic 124, such as accepting information in partial exchange for the desired subscription about the context of the use of a health regimen (such as the weather conditions and/or the mental condition of the user), and/or about an intention of the use of the health regimen (such as a description of the condition the intended use is designed to address), possibly including continuing updates of additional information to permit ongoing monitoring of information about the use of a health regimen, where the health regimen information is stored on computer 108 and/or computer 118 and/or computer 126). Operation 1408 illustrates accepting an endorsement (e.g., accepting an endorsement, via an end-user interface device 104 and/or vendor interface device 114 and/or publisher interface device 112 and end-user logic 106 and/or vendor logic 116 and/or publisher logic 124, such as accepting endorsement concerning the use of a health regimen in return for the desired subscription, where the health regimen information is stored on computer 108 and/or computer 118 and/or computer 126).

Figure 15:
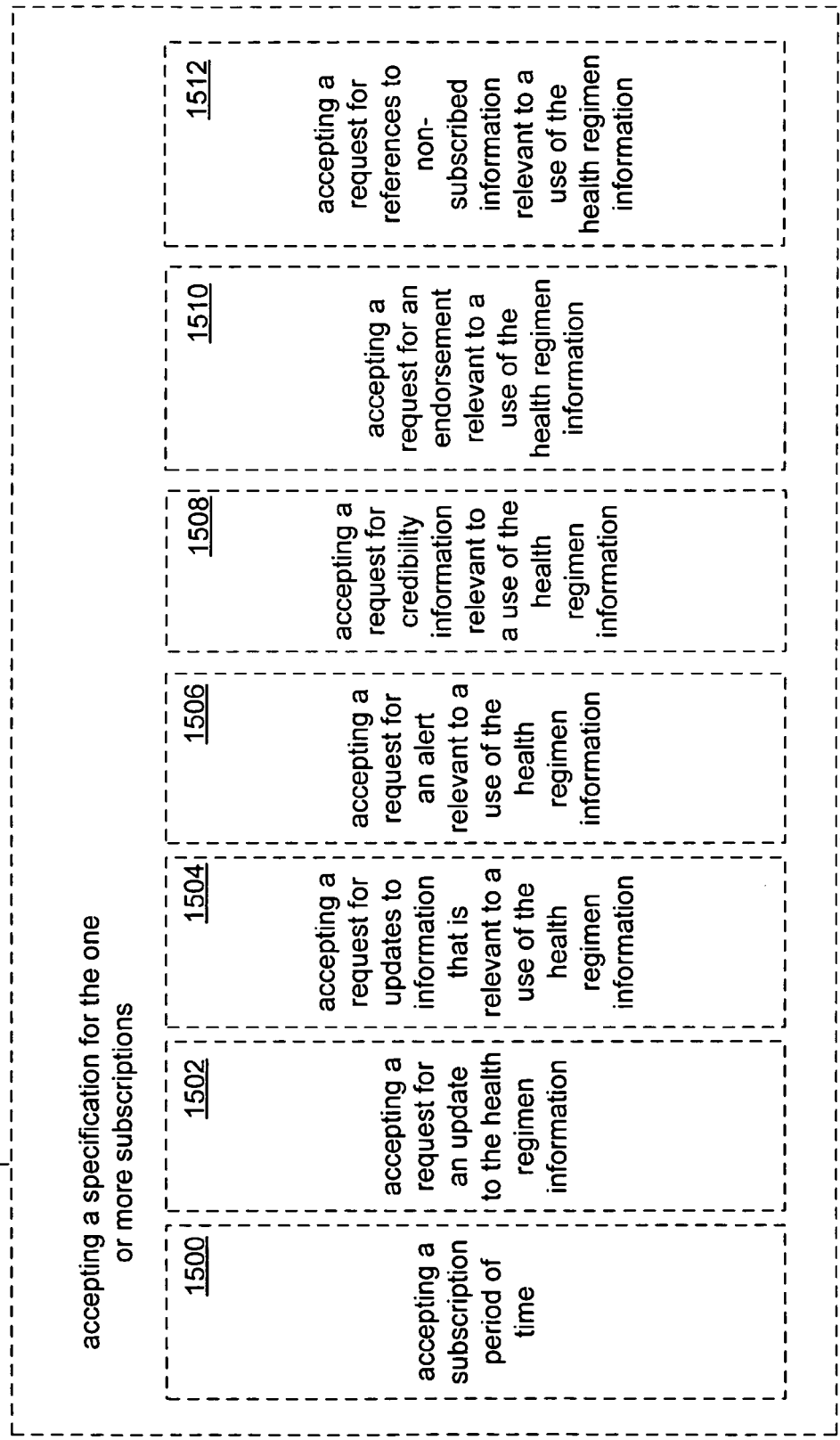
FIG. 15 shows several alternative implementations of the high-level logic flowchart of FIG. 13.

FIG. 15 depicts several alternative implementations of the high-level logic flowchart of FIG. 13. Operation 1302—accepting a specification for the one or more subscriptions—may include one or more of the following operations: 1500, 1502, 1504, 1506, 1508, 1510, and/or 1512. Operation 1500 shows accepting a subscription period of time (e.g., accepting a subscription period of time, via an end-user interface device 104 and/or vendor interface device 114 and/or publisher interface device 112 and end-user logic 106 and/or vendor logic 116 and/or publisher logic 124, such as accepting the specification of a period of time during which the subscription is to be active, where the health regimen information is stored on computer 108 and/or computer 118 and/or computer 126). Operation 1502 depicts accepting a request for an update to the health regimen information (e.g., accepting a request for an update to the health regimen information, via an end-user interface device 104 and/or vendor interface device 114 and/or publisher interface device 112 and end-user logic 106 and/or vendor logic 116 and/or publisher logic 124, such as accepting a request for the health regimen information to be received under the subscription to be updated as improvements to the health regimen are discovered and/or detected, where the health regimen information is stored on computer 108 and/or computer 118 and/or computer 126).

Operation 1504 illustrates accepting a request for updates to information that is relevant to a use of the health regimen information (e.g., accepting a request for updates to information that is relevant to a use of the health regimen information, via an end-user interface device 104 and/or vendor interface device 114 and/or publisher interface device 112 and end-user logic 106 and/or vendor logic 116 and/or publisher logic 124, such as accepting a request for health regimen information to be received under the subscription, where the health regimen information may show advantages and/or drawbacks to the use of the information provided and/or to be provided under the subscription, where the health regimen information is stored on computer 108 and/or computer 118 and/or computer 126). Operation 1506 shows accepting a request for an alert relevant to a use of the health regimen information (e.g., accepting a request for an alert relevant to a use of the health regimen information, via an end-user interface device 104 and/or vendor interface device 114 and/or publisher interface device 112 and end-user logic 106 and/or vendor logic 116 and/or publisher logic 124, such as accepting a request for health regimen information to be received under the subscription, where the health regimen information may show dangers to the use of the information provided and/or to be provided under the subscription, where the health regimen information is stored on computer 108 and/or computer 118 and/or computer 126). Operation 1508 shows accepting a request for credibility information relevant to a use of the health regimen information (e.g., accepting a request for credibility information relevant to a use of the health regimen information, via an end-user interface device 104 and/or vendor interface device 114 and/or publisher interface device 112 and end-user logic 106 and/or vendor logic 116 and/or publisher logic 124, such as accepting a request for a credibility rating on a scale of 0 to 10, with 0 representing an absence of reasons to give weight to the health regimen information to be received under the subscription and 10 representing a predetermined number of endorsements from trusted authorities and/or reports of scientifically conducted studies confirming the health regimen information to be received under the subscription, where the health regimen information is stored on computer 108 and/or computer 118 and/or computer 126). Operation 1510 shows accepting a request for an endorsement relevant to a use of the health regimen information (e.g., accepting a request for an endorsement relevant to a use of the health regimen information, via an end-user interface device 104 and/or vendor interface device 114 and/or publisher interface device 112 and end-user logic 106 and/or vendor logic 116 and/or publisher logic 124, such as accepting a request for an endorsement of the health regimen information to be received under the subscription, including but not limited to an expert endorsement and/or an endorsement from a trusted authority, where the health regimen information is stored on computer 108 and/or computer 118 and/or computer 126). Operation 1512 shows accepting a request for references to non-subscribed information relevant to a use of the health regimen information (e.g., accepting a request for references to non-subscribed information relevant to a use of the health regimen information, via an end-user interface device 104 and/or vendor interface device 114 and/or publisher interface device 112 and end-user logic 106 and/or vendor logic 116 and/or publisher logic 124, such as accepting a request for information not provided under the subscription, including but not limited to research reports on a particular substance, the use of which is included in the subscribed information, where the health regimen information is stored on computer 108 and/or computer 118 and/or computer 126).

Figure 16:
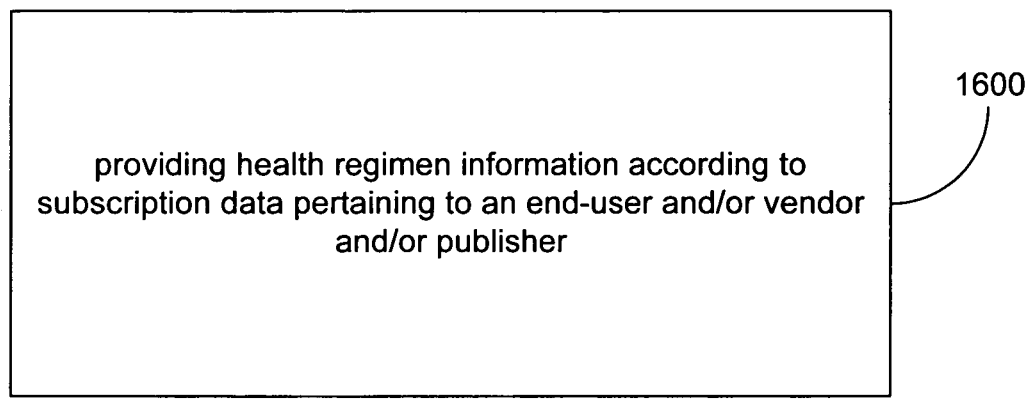
FIG. 16 depicts a high-level logic flowchart of an operational process.

FIG. 16 depicts a high-level logic flowchart of an operational process. Operation 1600 shows providing health regimen information according to subscription data pertaining to an end-user and/or vendor and/or publisher (e.g., providing health regimen information according to subscription data pertaining to an end-user and/or vendor and/or publisher, via an end-user interface device 104 and/or vendor interface device 114 and/or publisher interface device 112 and end-user logic 106 and/or vendor logic 116 and/or publisher logic 124, such as providing health regimen information to an end-user and/or vendor and/or publisher for a period of time specified for the end-user and/or vendor and/or publisher, where the health regimen information is stored on computer 108 and/or computer 118 and/or computer 126).

Figure 17:
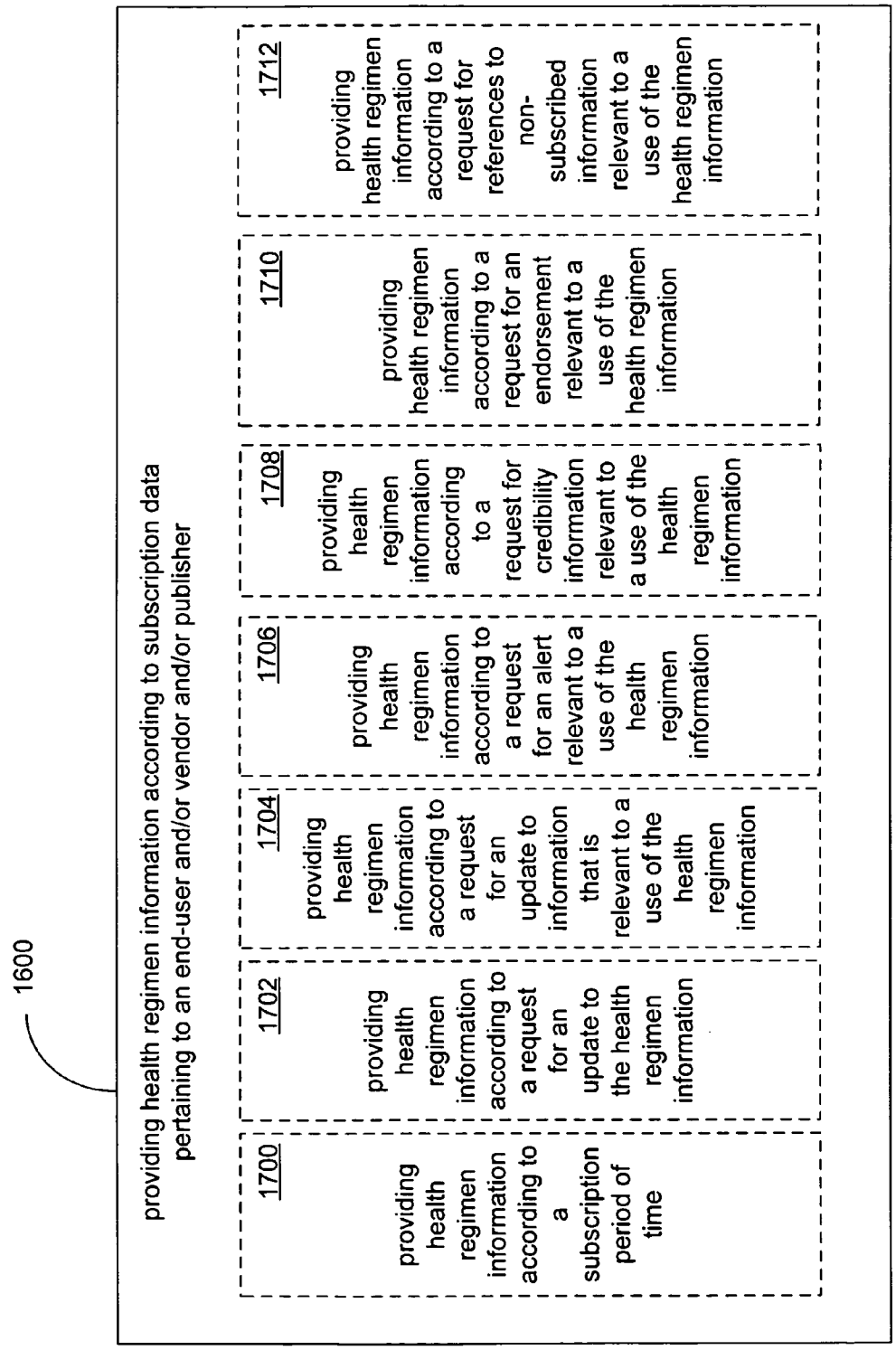
FIG. 17 shows several alternative implementations of the high-level logic flowchart of FIG. 16.

FIG. 17 depicts several alternative implementations of the high-level logic flowchart of FIG. 16. Operation 1600—providing health regimen information according to subscription data pertaining to an end-user and/or vendor and/or publisher—may include one or more of the following operations: 1700, 1702, 1704, 1706, 1708, 1710, and/or 1712.

Operation 1700 shows providing health regimen information according to a subscription period of time (e.g., providing health regimen information according to a subscription period of time, via an end-user interface device 104 and/or vendor interface device 114 and/or publisher interface device 112 and end-user logic 106 and/or vendor logic 116 and/or publisher logic 124, such as providing health regimen information to an end-user and/or vendor and/or publisher for a period of time specified for the end-user and/or vendor and/or publisher, where the health regimen information is stored on computer 108 and/or computer 118 and/or computer 126).

Operation 1702 depicts providing health regimen information according to a request for an update to the health regimen information (e.g., providing health regimen information according to a request for an update to the health regimen information, via an end-user interface device 104 and/or vendor interface device 114 and/or publisher interface device 112 and end-user logic 106 and/or vendor logic 116 and/or publisher logic 124, such as providing updated health regimen information as improvements to the health regimen are discovered and/or detected, where the health regimen information is stored on computer 108 and/or computer 118 and/or computer 126).

Operation 1704 illustrates providing health regimen information according to a request for an update to information that is relevant to a use of the health regimen information (e.g., providing health regimen information according to a request for an update to information that is relevant to a use of the health regimen information, via an end-user interface device 104 and/or vendor interface device 114 and/or publisher interface device 112 and end-user logic 106 and/or vendor logic 116 and/or publisher logic 124, such as providing health regimen information that may show advantages and/or drawbacks to the use of the information provided and/or to be provided under the subscription, where the health regimen information is stored on computer 108 and/or computer 118 and/or computer 126).

Operation 1706 shows providing health regimen information according to a request for an alert relevant to a use of the health regimen information (e.g., providing health regimen information according to a request for an alert relevant to a use of the health regimen information, via an end-user interface device 104 and/or vendor interface device 114 and/or publisher interface device 112 and end-user logic 106 and/or vendor logic 116 and/or publisher logic 124, such as providing health regimen information that may show dangers to the use of the information provided and/or to be provided under the subscription, where the health regimen information is stored on computer 108 and/or computer 118 and/or computer 126).

Operation 1708 shows providing health regimen information according to a request for credibility information relevant to a use of the health regimen information (e.g., providing health regimen information according to a request for credibility information relevant to a use of the health regimen information, via an end-user interface device 104 and/or vendor interface device 114 and/or publisher interface device 112 and end-user logic 106 and/or vendor logic 116 and/or publisher logic 124, such as providing information that indicates the credibility of the health regimen information to be received under the subscription, including but not limited to a rating of credibility from a trusted authority, where the health regimen information is stored on computer 108 and/or computer 118 and/or computer 126).

Operation 1710 shows providing health regimen information according to a request for an endorsement relevant to a use of the health regimen information (e.g., providing health regimen information according to a request for an endorsement relevant to a use of the health regimen information, via an end-user interface device 104 and/or vendor interface device 114 and/or publisher interface device 112 and end-user logic 106 and/or vendor logic 116 and/or publisher logic 124, such as providing health regimen information under the subscription, including but not limited to an expert endorsement and/or an endorsement from a trusted authority, where the health regimen information is stored on computer 108 and/or computer 118 and/or computer 126).

Operation 1712 shows providing health regimen information according to a request for references to non-subscribed information relevant to a use of the health regimen information (e.g., providing health regimen information according to a request for references to non-subscribed information relevant to a use of the health regimen information, via an end-user interface device 104 and/or vendor interface device 114 and/or publisher interface device 112 and end-user logic 106 and/or vendor logic 116 and/or publisher logic 124, such as providing additional information at additional cost, not to be provided under the subscription, including but not limited to research reports on a particular substance, the use of which is included in the subscribed information, where the health regimen information is stored on computer 108 and/or computer 118 and/or computer 126).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

We claim:

1. A method for a computer processor related to health-related data management, the method comprising:
   providing health regimen information by the computer processor, according to subscription data pertaining to an end-user and/or vendor and/or publisher, the health regimen information to be linked by associative information and stored in one or more computer readable memories at end-user's and/or vendor's and/or publisher's computer;

providing credibility data and endorsement data by the computer processor as the health regimen data, the credibility data and the endorsement data comprising at least a rating on a numeric scale, the numeric scale associated with one or more rankings that range from an absence of a reason to give a weight to the health regimen information received according to the subscription data to a predetermined number of endorsements from one or more trusted authorities;

confirming the health regimen information by patterns and correlations found between two or more health regimen data entities to provide the end-user and/or the vendor and/or the publisher with the health regimen information conforming to the accepted subscription data for the one or more subscriptions; and providing one or more subscriptions in a partial exchange for accepting additional information via an end-user interface device and/or a vendor interface device and/or a publisher interface device; and providing the additional information via an end-user interface device and/or the vendor interface and/or the publisher interface device at an additional cost to the one or more subscriptions.

2. A system related to health-related data management, the system comprising:
   a processor configured to:
      accept subscription data for one or more subscriptions for provision of health regimen information from an end-user and/or vendor and/or publisher, the health regimen information to be linked by associative information and stored in one or more computer readable memories at end-user's and/or vendor's and/or publisher's computers; and
      accept additional information via an end-user interface device and/or a vendor interface device and/or a publisher interface device in partial exchange for one or more subscriptions; and
   a memory coupled to the processor configured to:
      find patterns and correlations between two or more health regimen data entities to provide the end-user and/or vendor and/or publisher with health regimen information conforming to the accepted subscription data for the one or more subscriptions including a credibility data identified by the correlations between the two or more health regimen data entities, the credibility data comprising at least a rating on a numeric scale, the numeric scale associated with one or more rankings that range from an absence of a reason to give a weight to the health regimen information received according to the subscription data to a predetermined number of endorsements from one or more trusted authorities; and
      provide, at an additional cost, according to a request for one or more references to a non-subscribed information relevant to a use of the health regimen information, the additional information provided via the end-user interface device and/or the vendor interface device and/or the publisher interface device, the use of which is included in the subscribed information.

3. A system related to health-related data management, the system comprising:
   a memory coupled to a processor configured to provide health regimen information according to subscription data pertaining to an end-user and/or vendor and/or publisher, the health regimen information to be linked by associative information and stored in one or more computer readable memories at end-user's and/or vendor's and/or publisher's computers to find patterns and correlations between health regimen data entities to enable identification of credibility data identified by the correlations between the two or more health regimen data entities, the credibility data comprising at least a rating on a numeric scale, the numeric scale associated with one or more rankings that range from an absence of a reason to give a weight to the health regimen information received according to the subscription data to a predetermined number of endorsements from one or more trusted authorities.

4. A system related to health-related data management, the system comprising:
   means for accepting subscription data for one or more subscriptions for provision of health regimen information from an end-user and/or vendor and/or publisher, the health regimen information to be linked by associative information and stored in one or more computer readable memories at end-user's and/or vendor's and/or publisher's computers; and
   means for finding patterns and correlations between two or more health regimen data entities to provide the end-user and/or vendor and/or publisher with health regimen information conforming to the accepted subscription data for the one or more subscriptions the patterns and correlations providing a credibility data related to the health regimen information, the credibility data comprising at least a rating on a numeric scale, the numeric scale associated with one or more rankings that range from an absence of a reason to give a weight to the health regimen information received according to the subscription data to a predetermined number of endorsements from one or more trusted authorities; and
   means for providing one or more subscriptions in a partial exchange for accepting additional information via an end-user interface device and/or a vendor interface device and/or a publisher interface device; and
   means for providing the additional information via the end-user interface device and/or the vendor interface and/or the publisher interface device at an additional cost to the one or more subscriptions.

5. A program product, comprising:
   a non-transitory computer-readable storage medium bearing:
   one or more computer executable instructions embodied on the computer-readable storage medium for:
      accepting subscription data for one or more subscriptions for provision of health regimen information from an end-user and/or vendor and/or publisher, the health regimen information to be linked by associative information and stored in multiple computer readable memories at end-user's and/or vendor's and/or publisher's computers; and
      finding patterns and correlations between two or more health regimen data entities to provide the end-user and/or vendor and/or publisher with health regimen information conforming to the accepted subscription data for the one or more subscriptions the patterns and correlations providing a credibility data related to the health regimen information, the credibility data comprising at least a rating on a numeric scale, the numeric scale associated with one or more rankings that range from an absence of a reason to give a weight to the health regimen information received according to the subscription data to a predetermined number of endorsements from one or more trusted authorities;

accepting additional information, via an end-user interface device and/or a vendor interface device and/or a publisher interface device;

providing, at an additional cost, the additional information according to a request for one or more references to non-subscribed information relevant to a use of the health regimen information, the additional information provided via the end-user interface device and/or the vendor interface device and/or the publisher interface device.

6. The program product of claim 5, wherein the one or more instructions for accepting subscription data for the one or more subscriptions for provision of health regimen information from an end-user and/or vendor and/or publisher further comprise:

one or more instructions for accepting a payment for the one or more subscriptions.

7. The program product of claim 6, wherein the one or more instructions for accepting a payment for the one or more subscriptions further comprise:

one or more instructions for accepting a monetary payment.

8. The program product of claim 6, wherein the one or more instructions for accepting a payment for the one or more subscriptions further comprise:

one or more instructions for accepting data authenticating an identity of a payer.

9. The program product of claim 6, wherein the one or more instructions for accepting a payment for the one or more subscriptions further comprise:

one or more instructions for accepting the additional information.

10. The program product of claim 6, wherein the one or more instructions for accepting a payment for the one or more subscriptions further comprise:

one or more instructions for accepting an endorsement.

11. The program product of claim 5, wherein the one or more instructions for accepting subscription data for one or more subscriptions for provision of health regimen information from an end-user and/or vendor and/or publisher further comprise:

one or more instructions for accepting a specification for the one or more subscriptions.

12. The program product of claim 11, wherein the one or more instructions for accepting a specification for the one or more subscriptions further comprise:

one or more instructions for accepting a subscription period of time.

13. The program product of claim 11, wherein the one or more instructions for accepting a specification for the one or more subscriptions further comprise:

one or more instructions for accepting a request for an update to the health regimen information.

14. The program product of claim 11, wherein the one or more instructions for accepting a specification for the one or more subscriptions further comprise:

one or more instructions for accepting a request for updates to information that is relevant to a use of the health regimen information.

15. The program product of claim 11, wherein the one or more instructions for accepting a specification for the one or more subscriptions further comprise:

one or more instructions for accepting a request for an alert relevant to a use of the health regimen information.

16. The program product of claim 11, wherein the one or more instructions for accepting a specification for the one or more subscriptions further comprise:

one or more instructions for accepting a request for an endorsement relevant to a use of the health regimen information.

17. A program product, comprising:

a non-transitory computer-readable storage medium bearing one or more computer executable instructions embodied on the computer-readable storage medium for:

providing health regimen information according to subscription data pertaining to an end-user and/or vendor and/or publisher, the health regimen information to be linked by associative information and stored in one or more computer readable memories at end-user's and/or vendor's and/or publisher's computers to find patterns and correlations between health regimen data entities and for providing a credibility data and an endorsement data as the health regimen data, the credibility data and the endorsement data comprising at least a rating on a numeric scale, the numeric scale associated with one or more rankings that range from an absence of a reason to give a weight to the health regimen information received according to the subscription data to a predetermined number of endorsements from one or more trusted authorities;

confirming the health regimen information by patterns and correlations found between the two or more health regimen data entities to provide the end-user and/or the vendor and/or the publisher with the health regimen information conforming to the accepted subscription data for the one or more subscriptions;

providing one or more subscriptions in a partial exchange for accepting additional information via an end-user interface device and/or a vendor interface device and/or a publisher interface device;

providing, at an additional cost, the additional information according to a request for one or more references to a non-subscribed information relevant to a use of the health regimen information, the additional information provided via the end-user interface device and/or the vendor interface device and/or the publisher interface device.

18. The program product of claim 17, wherein the one or more instructions for providing health regimen information according to subscription data pertaining to an end-user and/or vendor and/or publisher further comprise:

one or more instructions for providing health regimen information according to a subscription period of time.

19. The program product of claim 17, wherein the one or more instructions for providing health regimen information according to subscription data pertaining to an end-user and/or vendor and/or publisher further comprise:

one or more instructions for providing health regimen information according to a request for an update to the health regimen information.

20. The program product of claim 17, wherein the one or more instructions for providing health regimen information according to subscription data pertaining to an end-user and/or vendor and/or publisher further comprise:

one or more instructions for providing health regimen information according to a request for an update to information that is relevant to a use of the health regimen information.

21. The program product of claim 17, wherein the one or more instructions for providing health regimen information according to subscription data pertaining to an end-user and/or vendor and/or publisher further comprise:

one or more instructions for providing health regimen information according to a request for an alert relevant to a use of the health regimen information.

22. The program product of claim 17, wherein the one or more instructions for providing health regimen information according to subscription data pertaining to an end-user and/or vendor and/or publisher further comprise:
one or more instructions for providing health regimen information according to a request for an endorsement relevant to a use of the health regimen information.

* * * * *

UNITED STATES PATENT AND TRADEMARK OFFICE
CERTIFICATE OF CORRECTION

| | |
|---|---|
| PATENT NO. | : 8,468,029 B2 |
| APPLICATION NO. | : 11/314764 |
| DATED | : June 18, 2013 |
| INVENTOR(S) | : Jung et al. |

Page 1 of 1

It is certified that error appears in the above-identified patent and that said Letters Patent is hereby corrected as shown below:

In the Specification:

In Column 2, Lines 10-11 please delete text "[To be Assigned]" and replace with --11/314,949--

Signed and Sealed this
Twenty-fourth Day of September, 2013

Teresa Stanek Rea
*Deputy Director of the United States Patent and Trademark Office*